United States Patent
Eggink et al.

(10) Patent No.: US 8,496,942 B2
(45) Date of Patent: *Jul. 30, 2013

(54) THERAPEUTIC PEPTIDES AND USES THEREOF

(75) Inventors: Laura L. Eggink, Scottsdale, AZ (US); J. Kenneth Hoober, Phoenix, AZ (US)

(73) Assignee: Susavion Biosciences, Inc., Tempe, AZ (US)

( * ) Notice: Subject to any disclaimer, the term of this patent is extended or adjusted under 35 U.S.C. 154(b) by 302 days.

This patent is subject to a terminal disclaimer.

(21) Appl. No.: 12/823,560

(22) Filed: Jun. 25, 2010

(65) Prior Publication Data

US 2010/0285003 A1  Nov. 11, 2010

Related U.S. Application Data

(63) Continuation-in-part of application No. 11/955,226, filed on Dec. 12, 2007, now Pat. No. 7,811,995.

(60) Provisional application No. 61/221,019, filed on Jun. 26, 2009, provisional application No. 60/974,056, filed on Sep. 20, 2007, provisional application No. 60/869,865, filed on Dec. 13, 2006.

(51) Int. Cl.
*A61K 38/08* (2006.01)
*A61K 39/39* (2006.01)
*C07K 7/06* (2006.01)

(52) U.S. Cl.
USPC .................. 424/278.1; 514/21.7; 530/328

(58) Field of Classification Search
None
See application file for complete search history.

(56) References Cited

U.S. PATENT DOCUMENTS

| 5,358,934 | A | * | 10/1994 | Borovsky et al. ............... 514/4.5 |
| 5,559,209 | A | * | 9/1996 | Nishimoto ..................... 530/326 |
| 5,641,747 | A | | 6/1997 | Popoff et al. |
| 5,753,481 | A | | 5/1998 | Niwa et al. |
| 6,193,981 | B1 | | 2/2001 | Goldstein |
| 6,498,020 | B1 | | 12/2002 | Walker et al. |
| 6,551,795 | B1 | | 4/2003 | Rubenfield et al. |
| 7,811,995 | B2 | * | 10/2010 | Eggink et al. .................. 514/3.8 |
| 2004/0123343 | A1 | | 6/2004 | La Rosa et al. |
| 2004/0248192 | A1 | | 12/2004 | Marchalonis et al. |
| 2005/0063937 | A1 | | 3/2005 | Li et al. |
| 2006/0078535 | A1 | | 4/2006 | Livant |
| 2006/0148093 | A1 | | 7/2006 | Gygi et al. |

(Continued)

FOREIGN PATENT DOCUMENTS

| CA | 2290722 A1 | 6/2001 |
| JP | 2003070481 A * | 3/2003 |

(Continued)

OTHER PUBLICATIONS

Machine Translation of JP 2003070481 A (Mar. 2003).*

(Continued)

*Primary Examiner* — Jeffrey E Russel
(74) *Attorney, Agent, or Firm* — Rodney J. Fuller; Booth Udall Fuller, PLC

(57) ABSTRACT

The present invention is directed to a family of therapeutic peptides capable of modulating cytokine expression and/or stimulating the immune system of subject without producing or sustaining serious side-effects. Methods using the peptides to modulate cytokine expression in a subject, treat a disease, enhance vaccination, and stimulate a subject's immune system response are also disclosed.

14 Claims, 9 Drawing Sheets

U.S. PATENT DOCUMENTS

| | | | |
|---|---|---|---|
| 2006/0189538 A1 | 8/2006 | Secombes et al. | |
| 2006/0269519 A1 | 11/2006 | Chen et al. | |
| 2007/0003542 A1 | 1/2007 | Zimmerman et al. | |
| 2008/0102076 A1 | 5/2008 | Eggink et al. | |
| 2008/0292650 A1* | 11/2008 | Eggink et al. | 424/185.1 |
| 2009/0041793 A1 | 2/2009 | Eggink et al. | |

FOREIGN PATENT DOCUMENTS

| | | |
|---|---|---|
| WO | 96/40903 | 12/1996 |
| WO | 00/31130 | 6/2000 |
| WO | 02/058589 | 8/2002 |
| WO | 03/091275 | 11/2003 |
| WO | 2004/011650 | 2/2004 |
| WO | 2005/087793 | 9/2005 |
| WO | 2006/063028 | 6/2006 |

OTHER PUBLICATIONS

Chargelegue et al., "A Peptide Mimic of a Protective Epitope of Respiratory Syncytial Virus Selected from a Combinatorial Library Induces Virus-Neutralizing Antibodies and Reduces Viral Load in Vivo," *J. of Virology*, 72(3):2040-2046 (Mar. 1998).

Ciesielski et al., "Cellular antitumor immune response to a branched lysine multiple antigenic peptide containing epitopes of a common tumor-specific antigen in a rat glioma model," *Cancer Immunol. Immunother.*, 54:107-119 (2005).

Chersi et al., "Specificities of rabbit antisera to multiple antigen (MAP) peptides," *J. of Biosciences*, 50(9-10):735-738 (Sep. 1, 1995) Abstract Only.

Cohen, J., "Hope on New AIDS Drugs, but Breast-Feeding Strategy Backfires," *Science*, 315:1357 (2007).

Eggink et al., "A biologically active peptide mimetic of N-acetylgalactosamine/galactose," *BMC Research Notes*, 2:23 (2009).

European Search Report for European Patent Application No. 07869233.2 dated May 11, 2010.

Fätkenheuer, G. et al., "Efficacy of Short-Term Monotherapy with Maraviroc, a New CRC5 Antagonist, in Patients Infected with HIV 1," *Nature Med.*, 11:1170-1172 (2005).

Glaxosmithkline, (2005a) "Study of Chemokine Coreceptor 5 (CCR5) Antagonist GW873140 in R5-Tropic Treatment-Experienced HIV Infected Subjects," ClinicalTrials.gov (Sep. 13, 2005) Identifier: NCT00197145S, (Terminated in 2005).

Glaxosmithkline, (2005b) "GlaxoSmithKline Halts Trials of Experimental CCR5 Inhibitor Aplaviroc in Treatment-naive HIV Patients Due to Concerns about Liver Toxicity," Statement to HIV Patient Community: Information from GlaxoSmithKline on Changes to Studies of Investigational CCR5 Entry Inhibitor Aplaviroc (GW873140) (Sep. 15, 2005), pp. 1-2.

International Search Report for PCT/US2005/003766 dated Apr. 5, 2006.

International Search Report for PCT/US2005/044215 dated Nov. 16, 2006.

International Search Report for PCT/US2007/87425 dated Aug. 5, 2008.

Latham, P.W., "Therapeutic Peptides Revisited," *Nature Biotech*, 17:755-757 (1999).

Manki et al., "Vaccination with Multiple Antigen Peptide as Rejection Antigen Peptide in Murine Leukemia," *Cancer Res.*, 58:1960-1964 (May 1, 1998).

Nicolaus, "Symbiotic Approach to Drug Design," *Decision Making in Drug Research*, pp. 173-186 (Jan. 1, 1983).

Olszewska et al., "Protection against Measles Virus-Induced Encephalitis by Anti-mimotope Antibodies: The Role of Antibody Affinity," *Virology*, 272(1):98-105 (Jun. 20, 2000).

Sarig, et al., "Telomeric and Tetraplex DNA Binding Properties of qTBP42: A Homoloque of the CArG Box Binding Protein CBF-A," *Biochem. and Biophys. Res. Comm*, 237(3):617-623 (1997).

Stover, J. et al., "The Global Impact of Scaling up HIV/AIDS Prevention Programs in Low- and Middle-Income Countries," *Science*, 311:1474-1476 (2006).

Supplementary European Search Report for European Application No. 07871699.0 dated May 17, 2010.

Written Opinion of the International Searching Authority for PCT/US2005/003766 dated Apr. 5, 2006.

Written Opinion of the International Searching Authority for PCT/US2005/044215 dated Nov. 16, 2006.

Written Opinion of the International Searching Authority for PCT/US2007/087413 dated Jul. 29, 2008.

Written Opinion of the International Searching Authority for PCT/US2007/087425 dated Aug. 5, 2008.

Office Action dated Oct. 23, 2012 in Japanese Application No. 2009-541593 (English translation) (6 pages).

\* cited by examiner

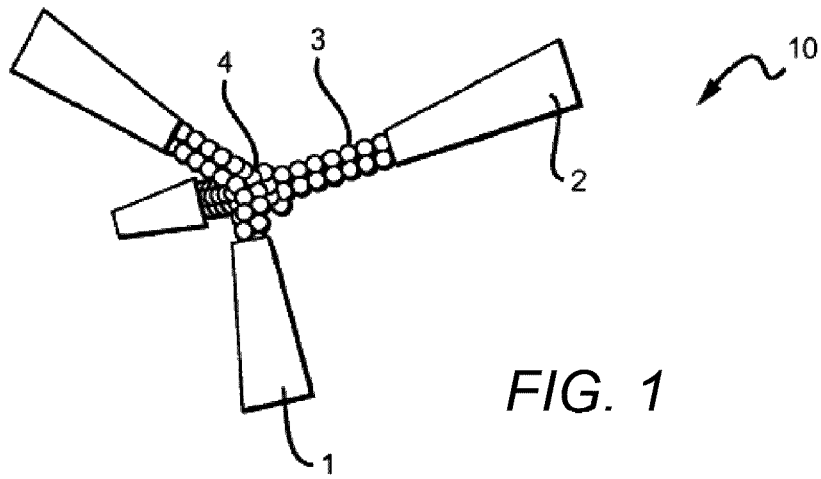
FIG. 1
FIG. 2A
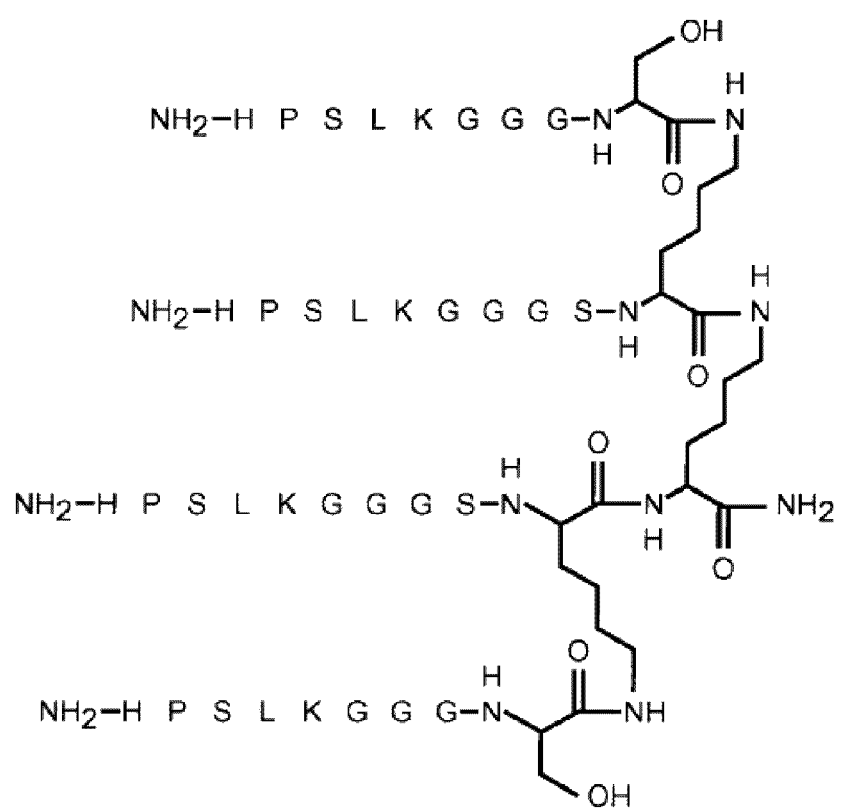

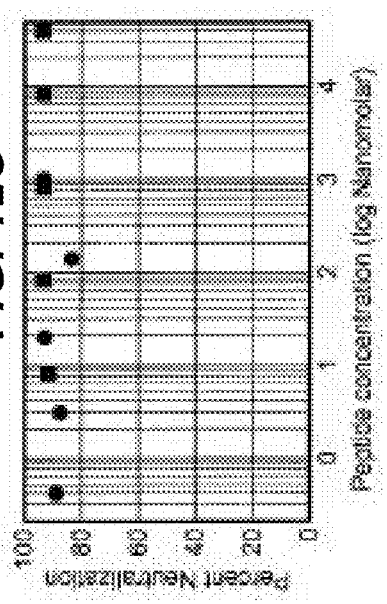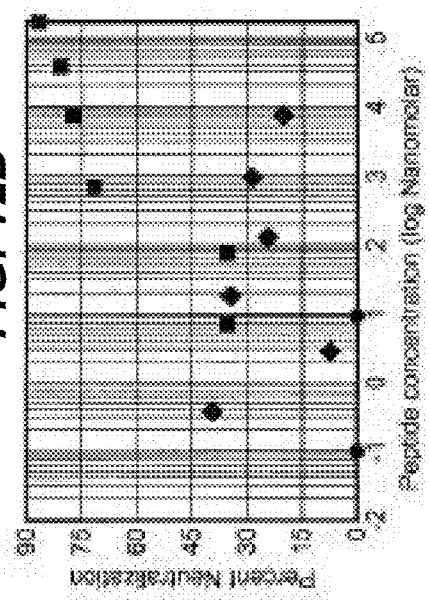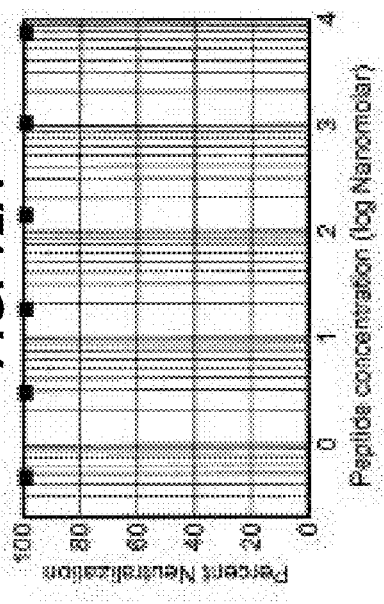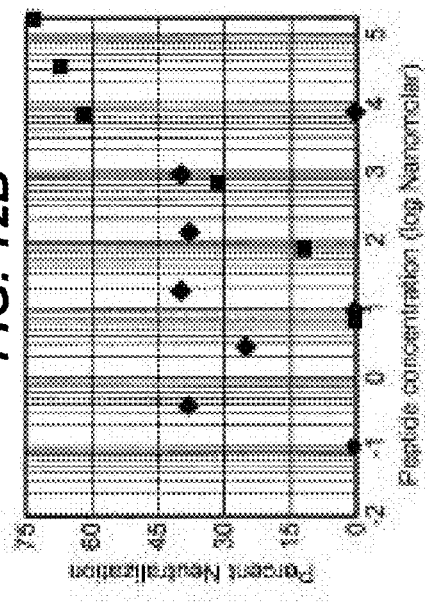

SEQUENCE LISTING

<160> NUMBER OF SEQ ID NOS: 13

<210> SEQ ID NO 1
<211> LENGTH: 5
<212> TYPE: PRT
<213> ORGANISM: Artificial Sequence
<220> FEATURE:
<223> OTHER INFORMATION: Synthetic Sequence

```
<400> SEQUENCE: 1

Val Gly Gly Gly Ser
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 2

Pro Ser Ser Asn Ala
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 3

His Pro Ser Leu Lys
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 4

His Pro Ser Leu Gly
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 5

His Pro Ser Leu Leu
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 6

His Pro Ser Leu Ala
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 7
```

Asn Pro Ser His Pro Leu Ser Gly
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 8

Asn Pro Ser His Pro Ser Leu Gly
1               5

<210> SEQ ID NO 9
<211> LENGTH: 4
<212> TYPE: PRT
<213> ORGANISM: Artificial Sequence
<220> FEATURE:
<223> OTHER INFORMATION: linker sequence

<400> SEQUENCE: 9

Gly Gly Gly Ser
1

<210> SEQ ID NO 10
<211> LENGTH: 8
<212> TYPE: PRT
<213> ORGANISM: Artificial Sequence
<220> FEATURE:
<223> OTHER INFORMATION: linker sequence

<400> SEQUENCE: 10

Gly Gly Gly Ser Gly Gly Gly Ser
1               5

<210> SEQ ID NO 11
<211> LENGTH: 4
<212> TYPE: PRT
<213> ORGANISM: Artificial Sequence
<220> FEATURE:
<223> OTHER INFORMATION: linker peptide

<400> SEQUENCE: 11

Ser Ser Ser Ser
1

<210> SEQ ID NO 12
<211> LENGTH: 8
<212> TYPE: PRT
<213> ORGANISM: Artificial Sequence
<220> FEATURE:
<223> OTHER INFORMATION: linker peptide

<400> SEQUENCE: 12

Ser Ser Ser Ser Ser Ser Ser Ser
1               5

<210> SEQ ID NO 13
<211> LENGTH: 5
<212> TYPE: PRT
<213> ORGANISM: Artificial Sequence -continued

```
<220> FEATURE:
<223> OTHER INFORMATION: Synthetic Sequence

<400> SEQUENCE: 13

Val Asn Ser Gln His
1               5
```

THERAPEUTIC PEPTIDES AND USES THEREOF

CROSS REFERENCE TO RELATED APPLICATIONS

The present application is related to and claims the benefit of U.S. Provisional Application No. 61/221,019, filed Jun. 26, 2009, and is a continuation-in-part of U.S. patent application Ser. No. 11/955,226, filed Dec. 12, 2007, which in turn claims the benefit of U.S. Provisional Application Nos. 60/974,056 filed Sep. 20, 2007 and 60/869,865 filed Dec. 13, 2006, the contents of each of which are incorporated herein by reference thereto.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 2531 byte ASCII (text) file named "Seq_List" created on Jun. 25, 2010.

FIELD OF THE INVENTION

The present invention is directed to therapeutic peptides and their uses in modulating endogenous cytokine expression and phagocytosis in a subject and/or immune system stimulation.

BACKGROUND

Approximately 40 million people are infected with HIV world-wide and 10% of these individuals will die each year from AIDS. In addition, the annual number of new infections is estimated to be 5 million and rising. The cost of treating this disease is enormous, and varies from $2,500 per patient in Brazil to over $15,000 per patient per year in developed countries. Cost of prevention is estimated at more than $120 billion over the next 10 years, although the long-term benefit from prevention would dramatically reduce future costs for treatment and care. The bulk of the cost of current treatment is for anti-retroviral drugs, which are remarkably effective but often lead to resistance. Furthermore, long-term control of the infection, most likely by management as a low-grade, chronic disease, increases the cost burden beyond that which can be afforded in low- and middle-income countries.

HIV-1 enters into cells by first attaching to one or more receptors on a cell, thereby inducing conformational and/or structural changes that allow insertion of the viral genome into the cell. Once inside the cell, the viral RNA genome is transcribed into DNA, integrated into the host genome, and then free to replicate. The primary therapies against HIV infections are anti-retroviral drugs that inhibit viral replication after entry into the cell. The most commonly used are nucleoside reverse transcriptase inhibitors, non-nucleoside reverse transcriptase inhibitors, and protease inhibitors that block enzymatic processing of viral products. These drugs effectively inhibit replication of the virus inside an infected cell and reduce viral load in the blood to undetectable levels.

Another therapeutic approach uses fusion inhibitors, including proteins (e.g. monoclonal antibodies), peptides and small molecule agents (e.g. drugs), some of which act on the outside of the cell to prevent HIV from fusing with and infecting it. If HIV cannot penetrate the host cell membrane and infect the cell, then HIV cannot replicate. Fusion inhibitors effectively block infection by HIV-1 and significantly reduce the systemic viral load. Vaccines that elicit antibodies that inhibit such fusion are of interest in this regard, and several pharmaceutical companies are working to achieve this goal.

Combinations of small molecular weight drugs, however, achieve undetectable levels of HIV virus in only about 50 to 60% of treated patients. In addition, the development of treatments that involve antibodies is generally costly and requires considerable medical infrastructure. Furthermore, although the development of prophylactic treatments such as vaccines is an important effort, particularly for susceptible target populations, this approach has thus far been unsuccessful. Protocols must be developed for those already infected.

In contrast to therapeutic approaches aimed at prevention or control of the disease by directly inhibiting a step in the viral replication cycle, as described above, reactivation of patients' immune system is an alternative therapy that holds promise for restoring health and productivity to an infected patient in a practical, cost-effective manner. As a result, an intense interest in immunotherapy, as indicated by the development of cytokine treatments for example, is leading to products that can stimulate or inhibit the immune system. One developmental cytokine/immunomodulator project for the treatment of HIV/AIDS has, for example, identified two key peptides derived from Thymus Nuclear Protein (TNP) technology (Viral Genetics, Inc., Azusa, Calif.), These peptides occur naturally in a variety of mammals, including humans.

The role of cytokines in the inhibition of HIV infectivity, particularly interleukin-16 (IL-16), interleukin-8 (IL-8) and RANTES (Regulated upon Activation, Normal T-cell Expressed, and Secreted; also known as CCL5), is very important. HIV-1 enters cells by first binding to two key molecular components on the cell surface, the protein CD4 and co-receptors CCR5 or CXCR4. CD4(−) cells are therefore insensitive to HIV, and genetic inactivation of CCR5 correlates strongly with resistance to HIV-1 infection. Cytokines such as IL-16, IL-8 and RANTES, which have overlapping and complementary functions, can act to attenuate viral infection by competing with viral binding and by interfering with viral entry into cells by down-regulating the receptors required for entry. Other cytokines such as interferons (e.g. IF-.alpha. and IF-.gamma.) act to reduce viral load by stimulating antibody-mediated phagocytosis.

Interleukins (IL's) and interferons (IF's) are potent cellular stimulants that are released from a variety of cells in response to insult or injury. Consequently, these proteins have attracted intense interest as therapeutic agents. However, similar to general stimulants such as lipopolysaccharide (LPS), IL's and IF's induce release of inflammatory cytokines and thus, when given at higher than normal concentrations during therapy, have substantial adverse effects resulting from inflammation which can be life-threatening and may require inpatient treatment facilities. Similarly, levels of TNF-α, IL-1β and IL-6 are directly correlated with the probability of death in humans. Moreover, production of recombinant IL's and IF's and their application are very costly, and even lower-dosage immunostimulant treatments developed for out-patient use have lower success rates and are not suitable in some situations such as, for example, to extend remission from cancer therapy or control a disease such as HIV at a chronic level.

In general, a stimulant of IL-8 and IL-16 release appears to be particularly suited for a role in enhancing host defense. Selective release of IL-8 by monocytes is possible without the release of inflammatory cytokines such as IL-1β and IL-6.

However, a potentially adverse effect of IL-8 production is the enhanced recruitment of neutrophils to inflamed endothelial cells and subsequent release of cytotoxic factors which cause cell/tissue damage, in addition to the continued production of IL-8 by adjacent (non-inflamed) endothelial cells. The consequence is a vicious cycle of recruitment of neutrophils in response to IL-8, damage to tissues, and more production of IL-8, although higher concentrations of IL-8 can be beneficial when they lead to internalization of receptors and de-sensitization of the cells. Therefore, exogenous therapeutic agents such as large, intact cytokine molecules are not well suited for general therapeutic use.

Information relevant to attempts to address one or more of these problems can be found in the following references: U.S. Patent Publication No. 2007/0003542; U.S. Patent Publication No. 2006/0269519; U.S. Patent Publication No. 2004/0248192; P. W. Latham, 1999; Fatkenheuer et al., 2005; Stover et al., 2006; Cohen, 2007; GlaxoSmithKline, 2005a and GlaxoSmithKline, 2005b. However, each one of these references suffers from one or more of the following disadvantages:

1. the size or composition of the agent provides significant challenges to cost-effective synthesis and purification;
2. the agent is specific for particular pathogen and/or cell type, rendering them unsuitable for general therapeutic use;
3. treatment with the agent induces clinically deleterious side effects that can be life-threatening, such as inflammation or hepatotoxicity, and require inpatient treatment facilities;
4. termination of treatment is followed soon thereafter by an increased systemic viral load;
5. long term exposure to agent often leads to treatment-resistant pathogens;
6. lower-dosage treatments developed for out-patient use have lower success rates and are not suitable in some situations;
7. treatment is ineffective, impractical, or cost-prohibitive for a large proportion of patients;
8. development of therapeutic antibodies require considerable medical infrastructure;
9. treatment such as vaccines may be appropriate to prevent infection but not to treat those already infected;
10. no beneficial synergy between the immunogenic response induced and the effects of other endogenous immunoregulators;
11. agent inhibits the release of inhibitory cytokines that suppress release of beneficial cytokines, an indirect treatment; and
12. agent acts to restore baseline cytokine levels to balance responses of the immune system rather than promoting activation of phagocytes.

Many of these therapeutic protocols also become ineffective with time because mutation of the pathogen allows it to escape the treatment. Moreover, any immunosuppression that accompanies the disease attenuates the ability of the innate immune system to respond to antigenic changes and thereby keep the infection under control. However, even though the virus may mutate at one or a few sites and thereby escape the neutralizing activity of antibodies, endogenously produced antibodies are usually polyclonal and may still bind the virus.

The immune system in individuals infected with a pathogenic agent such as HIV initiates a defense response by production of antibodies. The presence of anti-HIV antibodies is often used as a diagnostic test for infection. During the course of the disease, the antibody level remains high whereas the ability to maintain a minimal viral load gradually weakens as the population of CD4+ T cells declines. The cellular components of the innate immune response then become absent or quiescent. When the immune defense mechanisms reach a sufficiently low level, viral replication is not held in check and rapidly leads to a final stage of the disease, designated AIDS. However, even at this late stage, patients can be rescued from death by aggressive anti-retroviral therapy. Therefore, an agent that reactivates cells of the immune system, in particular phagocytes, will likely also restore an immune defense against progression of the disease.

In light of the available treatments for infections such as HIV induced AIDS, there are large numbers of people worldwide that need alternative, practical, cost-effective, non-specific therapies that directly bolster a patient's immune system during the course of the disease without causing deleterious side effects. Ideally, such therapies should also be effective against other types of pathogens.

Therapeutic agents that activate/reactive the immune system show particular promise in this regard, including cytokines and immunomodulators, although therapies based on exogenous agents such as large, intact cytokine molecules are not generally well suited for therapeutic use. Peptides, however, are often much more suitable therapeutic agents than large polypeptides or proteins. Peptides can, for example, be designed to induce one or more particular desired effects in vitro or in vivo, often without concomitantly inducing deleterious effects, and can usually be synthesized in a cost effective manner.

SUMMARY OF THE INVENTION

The present invention provides novel therapeutic peptides, and method for their use to modulate endogenous cytokine expression in a subject and/or to stimulate a subject's immune system. The therapeutic peptide consists of only 5 to 8 amino acids, and is selected from the group consisting of:

```
VGGGS                    (SEQ ID NO: 1)
and
X1-P-S-X2-X3-X4-X5-X6,
``` wherein X1 is selected from the group consisting of H and N, or is absent;
X2 is selected from the group consisting of L, S, N, and H;
X3 is selected from the group consisting of N, K, G, L, P, and A;
X4 is selected from the group consisting of A, S, and L, or is absent;
X5 is selected from the group consisting of S and L, or is absent;
X6 is G or is absent.

Preferably, the peptide is in substantially pure form. Typically it is desired that the peptide be at least 70%, more preferably at least 80%, and most preferably at least 85% pure by weight. In one embodiment the N-terminus may also be acetylated.

In a preferred embodiment, the peptides of the invention comprise a peptide construct with at least two arms. The construct typically has a central framework and each arm comprises a core sequence linked to the central framework via a linker. Each core sequence of the peptide construct can be the same or different. In a preferred embodiment, the core sequence is the same for each arm of peptide construct. The core sequence is preferably selected from the group of therapeutic peptides described above.

The present invention also provides a therapeutic compositions comprising at least one peptide of the invention and a pharmaceutically acceptable carrier. In a preferred embodiment, the composition is an immunostimulatory composition, preferably further comprising an antigen and/or an antibody preparation admixed therewith in an amount sufficient to enhance antibody-mediated cytotoxity or phagocytosis. Alternatively, the composition may comprise an immunoglobulin admixed with the therapeutic peptide in an amount sufficient to substantially enhance passive immune protection, e.g., at least 30%, 50%, or 80% increase compared to the control.

In yet another aspect of the invention, the invention provides a method of modulating the cytokine expression in a subject. The method preferably comprises administering to a subject one or more peptides of the invention in an amount sufficient to increase the expression of at least one beneficial endogenous cytokine and/or reduce expression of at least one harmful cytokine, for example the amount sufficient to increase expression of at least one beneficial endogenous cytokine or reduce expression of at least one harmful cytokine by at least 2 fold, more preferably at least 5 fold, and in certain embodiments at least 10 fold.

The peptides of the invention are useful in treating the subject having a disease, especially those diseases treatable by induction of antibodies against invading pathogens or endogenous antigens of harmful cells. The peptides of the invention can specifically be used to treat such diseases as HIV, cancer, bacterial and yeast infections, and/or other autoimmune diseases which require treatment through stimulation of the immune system.

The invention further encompasses methods of substantially inducing phagocytosis in a subject, preferably Fc-mediated phagocytosis to treat a subject. In a preferred embodiment, phagocytosis is increased in the subject by at least a 2 fold increase, more preferably by at least a 10 fold increase, and in certain preferred embodiments, at least a 20 fold increase.

BRIEF DESCRIPTION OF THE DRAWINGS

FIG. 1 illustrates a working model of the molecular structure of one embodiment of the invention, a multivalent immunoregulatory peptide construct containing four peptides according to the invention, each of which is linked to a central framework via a linker;

FIG. 2A illustrates the chemical structure of a peptide construct according to one embodiment of the invention, the construct containing four copies of the core sequence HPSLK (SEQ ID NO:3) linked to a branched central framework structure;

FIG. 12A is a scatter plot illustrating inhibition of HIV-1 clade B replication in human blood cells by the peptide construct containing four copies of the core sequence HPSLK (SEQ ID NO:3), in the presence of antiserum;

FIG. 12B is a scatter plot illustrating inhibition of HIV-1 clade B replication in human blood cells by the peptide construct containing four copies of the core sequence HPSLK (SEQ ID NO:3), in the absence of antiserum;

FIG. 12C is a scatter plot illustrating inhibition of HIV-1 clade C replication in human blood cells by the peptide construct containing four copies of the core sequence HPSLK (SEQ ID NO:3), in the presence of antiserum;

FIG. 12D is a scatter plot illustrating inhibition of HIV-1 clade C replication in human blood cells by the peptide construct containing four copies of the core sequence HPSLK (SEQ ID NO:3), in the absence of antiserum;

DETAILED DESCRIPTION OF THE PREFERRED EMBODIMENTS

Figure 2B:
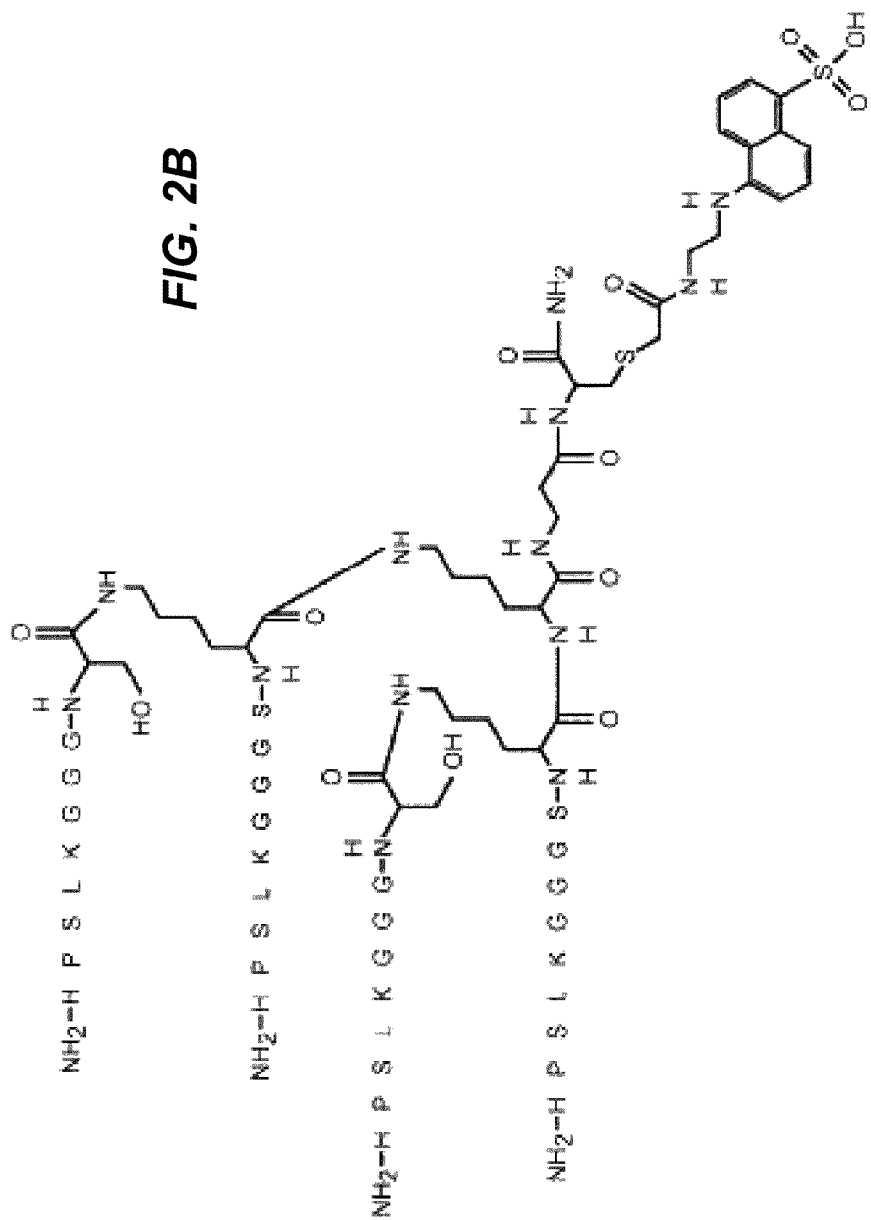
FIG. 2B illustrates the chemical structure of a peptide construct according to one embodiment of the invention, the construct as shown in FIG. 2A to which a dansyl tag has been added.

In order to provide a non-specific therapeutic agent with a relatively broad front, an agent that induces beneficial cytokine production should work in concert with the phagocytic activity of immune cells. The peptides of the present invention can accomplish this goal by concomitantly inducing the release of beneficial cytokines and stimulating the immune system, including phagocytes, to respond to the presence of pathogen-directed antibodies. Treatment with the peptides of the present invention should therefore induce activation of cells of the immune system in vivo and provide a sustained endogenous elevation of beneficial cytokines, in contrast to the rapid disappearance of these proteins when given exogenously.

Increases in the endogenous production of specifically IL-2, IL-8, IL-15, IL-16, and IL-21 should sustain an elevated level of beneficial cytokines that enhances the overall defense mechanism of the body without reaching concentrations that cause toxic side effects such as inflammation. Furthermore, selective cross-linking of cell-surface receptors by a multivalent structure incorporating at least one peptide of the present invention should act to attenuate viral infection by interfering with viral entry into cells and to stimulate activity of phagocytic cells to eliminate viral particles, thus enhancing treatment by minimizing or preventing further infection by active pathogens.

In the following description, and for the purposes of explanation, numerous specific details are set forth in order to provide a thorough understanding of the various aspects of the invention. It will be understood, however, by those skilled in the art, that the structures, compositions, and methods are sometimes shown or discussed generally in order to avoid obscuring the invention. In many cases, a description of the material and operation is sufficient to enable one to implement the various forms of the invention. It should be noted that there are many different and alternative technologies and treatments to which the disclosed inventions may be applied, and the full scope of the inventions is not limited to the examples that are described below. Unless otherwise defined, all technical and scientific terms used herein have the same meaning as commonly understood by one of ordinary skill in the art to which this invention belongs.

The present invention comprises therapeutic peptides, compositions of those therapeutic peptides for administration to a subject in need, and methods to stimulate the immune system of a subject through the administration of compositions containing those therapeutic peptides. In general, the advantage of this invention is the modulated release of specific cytokines and the stimulation of immune cells, including but not limited to phagocytes, to respond to the presence of pathogen-directed antibodies. Nonlimiting examples of cytokines include immunoregulatory proteins such as interleukins and interferons, which are secreted by cells of the immune system and can affect the immune response. A nonlimiting example of the stimulation of immune cells is the induction of Fc-mediated phagocytosis.

The single letter designation for amino acids is used predominately herein. As is well known by one of skill in the art, the single letter designations are as follows: A is alanine; C is cysteine; D is aspartic acid; E is glutamic acid; F is phenylalanine; G is glycine; H is histidine; I is isoleucine; K is lysine; L is leucine; M is methionine; N is asparagine; P is proline; Q is glutamine; R is arginine; S is serine; T is threonine; V is valine; W is tryptophan; Y is tyrosine.

The present invention identifies a series of polypeptides that stimulate immune response and modulate the release of specific cytokines Thus, in a first aspect, the present invention provides a therapeutic peptide consisting of 5 to 8 amino acids in length. In a preferred embodiment, the therapeutic peptide is in a substantially purified form. As used herein, the term "substantially purified" refers to material which is substantially or essentially free from components which normally accompany it as found in its native state. When the material is synthesized, the material is substantially or essentially free of cellular material, gel materials, culture medium, chemical precursors, contaminating polypeptides, nucleic acids, and other chemicals. Generally, the isolated or synthesized peptide will comprise more than 70% or 80% (dry weight) of all macromolecular species present in the preparation. Preferably, the peptide is purified to represent greater than 90% (dry weight) of all macromolecular species present. More preferably the peptide is purified to greater than 95% (dry weight), and most preferably the peptide is purified to essential homogeneity, wherein other macromolecular species are not detected by conventional techniques. Advantageously, the therapeutic peptide is reacted with acetic anhydride to acetylate the N-terminus of the therapeutic peptide. Acetylation stabilizes the peptide and therefore is preferred.

Preferred therapeutic peptides for this first aspect of the invention are selected from the group consisting of:

```
VGGGS                         SEQ ID NO: 1)
and
X1-P-S-X2-X3-X4-X5-X6,
``` wherein X1 is selected from the group consisting of H and N, or is absent;
X2 is selected from the group consisting of L, S, N, and H;
X3 is selected from the group consisting of N, K, G, L, P, and A;
X4 is selected from the group consisting of A, S, and L, or is absent;
X5 is selected from the group consisting of S and L, or is absent; and X6 is G, or is absent.

In a preferred embodiment,

X1 is N;
X2 is H;
X3 is P;
X4 and X5 are selected from the group consisting of S and L; and
X6 is G.

In another preferred embodiment,

X1 is H or is absent;
X2 is selected from the group consisting of L and N;
X3 is selected from the group consisting of A, K, G, and L; and
X4, X5, and X6 are absent.

In a further more specific preferred embodiment,

X1 is H;
X2 is selected from the group consisting of L and N;
X3 is selected from the group consisting of K, G, and L; and
X4, X5, and X6 are absent.

In a most preferred embodiment, the therapeutic peptide is selected from the group consisting of: VGGGS (SEQ ID NO:1), PSSNA (SEQ ID NO:2), HPSLK (SEQ ID NO:3), HPSLG (SEQ ID NO:4), HPSLL (SEQ ID NO:5), HPSLA (SEQ ID NO:6), NPSHPLSG (SEQ ID NO:7), and NPSHPSLG (SEQ ID NO:8).

In a second aspect, the present invention provides a therapeutic peptide comprising a construct and at least two arms, the construct having a central framework and each arm consisting of a core sequence linked to the central framework via a linker, wherein each core sequence is the same or different.

As used herein, "construct" is defined as the entire molecule and comprises the central framework linked with at least two arms. In a preferred embodiment, the construct comprises the central framework linked to 2 or more arms, e.g., 3, 4, 5, 6, 7, 8, 9, 10, 11, or 12 arms, preferably 2 to 8 arms. In a further preferred embodiment, the construct comprises the central framework linked to 4 arms. Each arm within the construct may consist of the same or different core sequence and/or linker. In one preferred embodiment, the core sequence is the same between arms.

The "central framework" is defined as the structural core of the construct, providing a structure for attaching the arms to a central structure. The central framework is based on a core molecule which has at least two functional groups to which molecular branches having terminal functional groups are bonded, e.g., a tri-lysine to which the peptide arms are added. Such molecules may be developed or created to present a varying number of branches, depending on the number of monomers branched from the core molecule. Each terminal functional group on each branch provides a means of attachment to an arm. Non-limiting examples of preferred central framework include: ethylenediamine (1,2-ethanediamine), ethylene glycol (1,2-dihydroxyethane), polyols such as glycerol, 3,5-diaminobenzoic acid, 1,3,5-triaminobenzene, and monocarboxylic-diamino compounds of intermediate length. Preferably, the monocarboxylic-diamino compounds are within the range of 2 to 10 carbons in length. Non-limiting examples of such compounds are 2,3-diaminopropionic acid and 2,6-diaminocaproic acid. In a more preferred embodiment, the monocarboxylic-diamino compound is 6 carbons in length. Compounds that provide an aromatic central framework which absorbs light may be beneficial for determining peptide concentration as well. The carboxyl group of the monocarboxylic-diamino compounds allows the addition of C-terminal tags including biotin derivatives. In a preferred embodiment, the central framework comprises a tri-lysine core (a lysine residue as the central molecule bonded to two lysine residues, each through its carboxyl group, to one of the amino groups of the central lysine residue), providing a central framework for four arms.

The "arm" is defined as the core sequence, defined below, plus the linker. The "linker" is defined as a peptide chain or other molecule that connects the central framework to the core sequence. In a preferred embodiment, the linker comprises, but is not limited to, certain linker peptide sequences, polyethylene glycol, 6-aminocaproic acid (6-aminohexanoic acid), 8-aminooctanoic acid, and dextran. In a most preferred embodiment, the linker is GGGS (SEQ ID NO:9), GGGSGGGS (SEQ ID NO:10), SSSS (SEQ ID NO:11), SSSSSSSS (SEQ ID NO:12), or variations thereof. The length of the linker can be adjusted, for example, the linker GGGS (SEQ ID NO:9) can be repeated to provide variable lengths, e.g., repeated twice (GGGSGGGS (SEQ ID NO:10)), or even three or more times; additional serine residues could be added to SSSS (SEQ ID NO:11) to also produce varying lengths of the linker.

The "core sequence" is defined as the functional portion of each arm that provides the therapeutic effect. The core sequence is preferably selected from the group of therapeutic peptides of 5 to 8 amino acids in length described above in the first aspect. In a most preferred embodiment, the core sequence is selected from the group consisting specifically of: VGGGS (SEQ ID NO:1), PSSNA (SEQ ID NO:2), HPSLK (SEQ ID NO:3), HPSLG (SEQ ID NO:4); HPSLL (SEQ ID NO:5), HPSLA (SEQ ID NO:6), NPSHPLSG (SEQ ID NO:7), and NPSHPSLG (SEQ ID NO:8).

A specific illustration of a multivalent immuno-regulatory peptide construct 10 is set forth in FIG. 1. The construct 10 can be synthesized with at least two arms 1, (e.g., two, three, four, eight or more arms 1). The same core peptide sequence 2 can be used for each arm or, alternatively, two or more different core peptide sequences can be used instead. The length of the linker 3 between the central framework 4 of the construct 10 and the core peptide sequence 2 determines the length of the arm 1. The arms 1 illustrated in FIG. 1, for example, are often about 3±0.5 nm in length depending on conformation, or approximately 7±0.5 nm across the molecule. Cell-surface domains of known receptor proteins are correspondingly about 3 to 4 nm in diameter. This distance can be adjusted by increasing or decreasing the length of the linker 3. Preferably, the length of each of the linkers 3 are designed to allow for and promote cross-linking of receptors. The multidimensional nature of the structure illustrated in FIG. 1 was obtained using standard molecular modeling techniques.

In a third aspect, the present invention provides a pharmaceutical composition, comprising one or more of the therapeutic peptides disclosed herein. Preferably the compositions comprise a pharmaceutically acceptable carrier. As used herein the term "pharmaceutically acceptable" means approved by a regulatory agency of the Federal or state government or listed in the U.S. Pharmacopeia or other generally recognized pharmacopeia for use in animals, and more particularly in humans. There term "carrier" refers to a diluent, adjuvant, excipient, or vehicle with which an active ingredient is administered. Such pharmaceutical carriers can be liquids, such as water and oils, including those of petroleum, animal, vegetable or synthetic origin. Preferably, the pharmaceutically acceptable carrier comprises, but is not limited to, a saline solution, a polyether, and/or water. Examples of suitable carriers, include water, phosphate-buffered saline, sodium chloride solutions, polyethylenelglycol solutions, glycerol, carbapol gel, propylene glycol, methyl paraben, hydroxypropylmethyl cellulose, isopropyl myristate, etc. The type and amount of carrier is typically influenced by the route of administration. For example, when the peptides are administered via injection, preferably carriers include, for example, a phosphate-buffered saline solution having a pH between 6.5 and 7.5 (e.g., about 7.2) or a sodium chloride solution (e.g., 100-150 mM); whereas when administered via a patch, the carrier preferably comprises a polyethyleneglycol solution (e.g., 250 mg/mL of PEG8000), but may be composed of other suitable carriers, such as, carbopol gel base, propylene glycol, methyl paraben, ethyl paraben, HPMC gel base (Hydroxypropylmethyl cellulose), PEG 4000, PEG 300, DMSO, isopropyl myristate, mineral oil, white petrolatum, bees wax, and glycerine.

The compositions may further contain drug targeting agents, bioavailability enhancement agents, or active ingredients other than compounds of the invention, and provide for immediate or modified release. For example, the compositions of the invention may advantageously comprise a target antigen. In this embodiment, the inclusion of an antigen in the composition allows the therapeutic peptide to serve as an adjuvant to stimulate and enhance the immune response to the antigen presentation within the body of the subject. In an alternative embodiment, the composition of the invention further comprises an antibody preparation, preferably a monoclonal antibody preparation. The inclusion of an antibody preparation in the composition, with or without the antigen, enhances antibody-mediated cytotoxicity and/or phagocytosis. For example, the antibody preparation can be used to tag a target cell (e.g., tumor cell). After the target cell is tagged, the therapeutic peptide-activated macrophages would kill the target cell, (e.g., by engulfment or lysis). Non-limiting examples of specific antibody preparations that can be included in the composition include, for example, antibodies targeting myleiod leukemia, B-cell leukemia, non-Hodgkin's lymphoma, breast cancer, glioma, and melanoma. Preferably, the compositions of the invention comprising a target antigen and/or antibody preparation also enhance the effectiveness of passive immune protection against diseases. Thus, for example, the compositions of the present invention could be used to enhance the effectiveness of passive immunity, e.g., rabies, tetanus, and hepatitis.

In another aspect of the invention, the invention provides a method of modulating the cytokine expression in a subject, as compared to the control and/or levels prior to administration of the peptide. The method preferably comprises administering to a subject one or more of the peptides of invention. The peptide is in an amount sufficient to increase the expression of at least one endogenous cytokine. Preferably the peptides stimulate, preferably substantially increase (e.g., by at least 40% compared to prior to administration), expression of at least one endogenous cytokine selected from the group consisting of: Eotaxin-2, ICAM-1, I-309, IL-2, IL-3, IL-4, IL-8, IL-15, IL-16, IL-17, IL-21, TNF-$\beta$, TIMP-2, RANTES, sTNF RI, and sTNF RII. Preferably, expression of IL-16 is stimulated by the peptide. Also, it is preferable if the administered peptides decrease at least one endogenous cytokine that induces inflammation. In a specific embodiment, the peptides decrease, preferably substantially decrease (e.g., by at least 20% compared to prior to administration), at least one cytokine selected from the group consisting of: IL-1$\alpha$, IL-11, IL-12p40, and IL-12p70. In this context, "substantially increase It is also preferable that the peptide does not substantially stimulate the release of IL-6. In this context, "does not substantially stimulate" means levels of IL-6 are not statistically greater (preferably, $p>0.20$, more preferably $p>0.10$; and most preferably $p>0.05$ or $p>0.1$) between treatments and control samples when examined in experiments similar to those described in Example 6. In a most preferred embodiment, administration of the therapeutic peptides does not induce systemic inflammation.

The present invention is also directed to methods of enhancing the immune system in a subject. The methods of the invention may advantageously be used to treat or prevent a disease in a subject. The methods of the invention typically increase and/or enhance antibody production against a target antigen or target cell. The method comprises the step of administering to a subject a composition of the invention described herein in an amount sufficient to treat the disease and/or stimulate the immune system of the subject. Stimulating the immune system preferably comprises producing immunogenic substances or agents, including for example, production of endogenous cytokines Preferably stimulation of the immune system using the compositions and methods described here also encompasses induction of phagocytosis and more specifically stimulation Fc-mediated phagocytosis in the subject.

Preferably the "amount sufficient" is the amount necessary to induce cytokine release and/or stimulate the immune system in a subject. In a more specific embodiment, the amount sufficient is an amount within the range of 1 pmole/g to 1 nmole/g of body weight and/or within the range of 0.1 to 300 mg per dose. For a typical adult human, the amount sufficient is usually within the range of 1 to 100 mg, more preferably, 2 to 70 mg, and most preferably 3 to 50 mg per dose, e.g. 5 to 20 mg. Based on the subjects body weight, preferably the amount is 0.01 to 1.4 mg/kg; 0.01 to 1 mg/kg; and most preferably between 0.02 to 0.7 mg/kg of the subject's body weight per dose. As a nonlimiting example, an amount sufficient to treat the disease in a typical 70 kg adult human would be 0.1 mg/kg of the subject's body weight, 2 µmole, or 7 mg per dose. As would be known to one skilled in the art, the lifetime of activated macrophages suggests that a dose should be administered once about every 2 to 6 days, more preferably 1 or 2 times a week, until the disease is treated, alleviating certain symptoms, and preferably by eradication from the body of the subject.

Preferably, the subject is an animal; more preferably, a mammal, e.g., monkey, dog, cat, horse, cow, sheep, pig; and most preferably a human.

Administration of the composition to the subject comprises transferring the composition into the body of the subject in an amount sufficient to treat the disease, including vaccination of the subject to the disease. The composition of the invention can be administered via any suitable route that achieves the intended purpose. For example, administration can be by subcutaneous, intravenous, intramuscular, intraperitoneal, buccal, or ocular routes, rectally, parenterally, intrasystemically, topically (as by powders, ointments, drops or transdermal patch), or as an oral or nasal spray. Alternatively, or concurrently, administration can be by the oral route. The dosage administered will be dependent upon the age, health, and weight of the recipient, kind of concurrent treatment, if any, frequency of treatment, and the nature of the effect desired.

In a preferred embodiment, the composition is administered orally. In this embodiment, the composition is in an edible form, including for example, powders, granules, capsules, pills, tablets, elixirs, suspensions, emulsions, syrups and the like. These preparations may be subjected to modification such as sustained-release, stabilization, easy disintegration, poor disintegration, enteric coating, easy absorption and the like. Preferably in this embodiment, the composition is in a form that allows for passage through the stomach and release in the intestine for absorption in intestinal lumen, e.g., enteric coated formations based on pH or timed release. Additionally, the dosage form may be in the form of chewable preparations, sublingual preparations, buccal preparations, troches, ointments, patches, solutions and the like. These preparations may be also subjected to modification such as sustained-release, stabilization, easy disintegration, poor disintegration, enteric coating, easy absorption and the like.

In another embodiment, the composition is administered via injection, e.g., subcutaneous, intramuscular, intravenous, and intraperitoneal injection, preferably subcutaneously. When the composition is formulated for transdermal administration, the composition preferably comprises PEG8000 in a medical patch. The patch preferably comprises 1 to 8 mg, more preferably 2 to 6 mg, and most preferably about 4 mg of therapeutic peptides per mL of solution in the patch. A patch typically comprises 1 to 75 mL, and more preferably 1 to 18 mL of solution within the patch. When administering to the subject, the patch should be in contact with the subject's skin for a period of at least 2 to 72 hours. A typical patch would be in contact with the subject's skin for approximately 24 to 48 hours.

It should be noted that the compositions and methods of the present invention are especially effective in treating those diseases in which activation of the subject's immune system is capable of producing antibodies in response to an antigen associated with the disease. Such diseases, for example, include proliferative diseases (e.g., cancer); microbial infections (e.g., bacterial or yeast infections); and viral infections (e.g., polio, influenza, rubella, hepatitis, including retroviral infections, such as HIV).

The present compositions are also effective at enhancing vaccination. In one embodiment, the invention is directed to a method of enhancing a vaccination. The method preferably comprises administering to a subject receiving a vaccination an effective amount of one or more peptides of the invention. The peptides should be administered to the subject in conjunction with the vaccination. This is typically at the same time or in the same composition with the vaccination, but administration would still be in conjunction with the vaccination if it was delivered separately, as long as the vaccination is systemically present while the immuno-stimulatory effects of peptides are still present in the subject. The peptide administered should be in an amount sufficient to stimulate the immune system of the subject to the vaccination. Stimulation is typically measured as compared to a control, the control preferably being vaccination of the subject without the peptide present.

In yet another aspect of the invention, the invention provides a diagnostic method for evaluating the potential effectiveness of a treatment for a subject, for example a subject having cancer or HIV, wherein the doctor is contemplating treating the subject with one or more peptides of the invention. The method preferably comprises: incubating a blood and/or cell sample from the subject. This is done in vitro in the presence of at least one therapeutic peptide of the invention as a test sample. The method also preferably includes incubating the blood and/or cell sample from the subject in the absence of the therapeutic peptide as a control. Finally, in this embodiment of the invention, the method further comprises measuring whether there is an increase in immunogenic activity in the test sample as compared to the control, wherein an increase immunogenic activity in the test sample is indicative of a potentially effective treatment for the subject. One example of a possible immunogenic activity that is preferably measured is whether there is an increase in phagocytic cell activity in the test sample.

The invention also is directed to a diagnostic method for evaluating the potential effectiveness of a treatment in subject, the method comprising: incubating a blood and/or cell sample from a subject in vitro in the presence of at least one therapeutic peptide according to claim 4; and measuring the production of cytokines released after incubation with the therapeutic peptide to obtain cytokine release results or measuring the activity of phagocytic cells in the sample to obtain phagocytic activity results. Preferably the cytokine release results and/or phagocytic activity results are used to determine whether the subject would likely respond effectively to treatment with the peptide.

EXAMPLES

The following examples illustrate, but do not limit, the compounds, methods and compositions of the present invention. Other suitable modifications and adaptations of the variety of conditions and parameters normally encountered in clinical therapy and which are obvious to those skilled in the art are within the spirit and scope of the invention.

Example 1

Peptide Design and Synthesis

Unique peptide sequences were designed by molecular modeling of docking to sugar-binding sites of lectins, downloaded from the Protein Data Bank (PDB), with ArgusLab 4.0.1 software (Mark A. Thompson, Planaria Software LLC, Seattle, Wash., http://www.arguslab.com). The corresponding peptides were synthesized by solid-phase methods using standard Fmoc side chain protection. Branched peptides were constructed on a central tri-lysine framework (Tam JP. 1996. Recent advances in multiple antigen peptides. Journal of Immunological Methods 196:17-32), which allows four identical sequences within the same structure. A linker, (GGGS, SEQ ID NO:9), was included to distance the core sequence from the central framework. Distances between the core sequences can be adjusted by decreasing or increasing the length of the linker, by including, without limitation, two linkers in tandem (GGGSGGGS, SEQ ID NO:10), or by inserting any suitable inert linker, including, without limitation, a polyethylene glycol (PEG) of a variable length. The branched structure was designed to have enhanced activity by causing receptor clustering (cross-linking) on the surface of responsive cells.

The peptides were synthesized on PAL-PEG-polystyrene resin (Applied Biosystems, Foster City, Calif.) utilizing Fmoc (9-fluorenylmethoxycarbonyl)-protected amino acids and a Milligen Biosearch 9050+ continuous flow peptide synthesizer (Millipore Corporation, Billerica, Mass.).

The C-terminus of the central framework is typically a lysine residue containing an amide derivative of the carboxyl group. However, the C-terminus can be modified to include additional C-terminal amino acids such as a cysteine residue, to which tags such as fluorescent groups can be added, or an ε-biotinyl-N-lysine (biotinyl-K) residue useful for subsequent purification processes. The availability of such sites can therefore be used to advantage in a number of ways, including, without limitation, to aid in detection, quantification, and purification of the peptides. In addition, an amino acid such as β-alanine (βA) or tryptophan can be inserted between the added C-terminal amino acid and the C-terminal lysine residue of the central framework in order to provide a spacer or a means to determine concentration by absorbance. Non-limiting examples of such modified C-terminal lysine residues on the central framework include K-βA-C and K-W-biotinyl-K, respectively. Furthermore, additional lysine residues can be added to either one or both of the α- and ε-amino groups of a modified C-terminal lysine on the central framework to yield, for example, (K)₂K, (K)₂K-βA-C or (K)₂K-W-biotinyl-K, thereby forming branched structures in which the α- and ε-amino groups are available for extension.

The lysine residues used at the branch points can be incorporated with Fmoc protection on both the α- and ε-amino groups, so that both become available for amide bond formation after the standard deprotection reaction with piperidine. In some embodiments, for example, a suitable fluorescent tag may be incorporated, including without limitation a dansyl group incorporated by reaction with the thiol group on the C-terminal cysteine using 5-((((2-iodoacetyl)amino)ethyl) amino)naphthalene-1-sulfonic acid (1,5-IAEDANS) following a standard protocol for thiol-reactive probes (Invitrogen Corp., Carlsbad, Calif.). Similarly, in these or other embodiments, biotin may be attached to lysine through an amide linkage to the side chain amino group which, because of its high affinity with streptavidin, provides a means to retrieve the peptide with associated proteins from reaction mixtures in order to study the interaction of the peptide with cellular components.

After cleavage from the resin bed, the product can be purified by HPLC on a preparative Jupiter Proteo C12 column (21.2 mm×250 mm) (Phenomenex, Inc., Torrance, Calif.) using a gradient from 8% to 18% acetonitrile in water containing 10 mM trifluoroacetic acid (TFA). The purity of the final peptide product was confirmed by mass spectroscopy performed using a Voyager DE STR mass spectrometer (Applied Biosystems, Foster City, Calif.). HPLC-purified peptide can be dried under vacuum, dissolved in sterile phosphate buffered saline, pH 7.2 (PBS) and passed through a gel filtration column of Sephadex G-15 or G-25 (1×48 cm for small samples) to separate TFA from the peptide. The column may then be eluted with sterile PBS. Endotoxin is removed by passage of the peptide through a column of DEAE-Sephadex A-25.

Alternatively, the product may be purified by other techniques, including without limitation the use of a $C_{18}$ reverse-phase cartridge, ion exchange chromatography, and gel filtration chromatography to remove side products of synthesis. Concentration can be determined by absorbance of the fluorophore (e.g., dansyl group, extinction coefficient, $\epsilon_{mM}$=5.7 cm$^{-1}$ at 336 nm), absorbance of the peptide bond at 210 nm ($\epsilon_{mg/mL}$≈31 cm$^{-1}$), absorbance of aromatic amino acids (e.g., tryptophan, $\epsilon_{mM}$=5.6 cm$^{-1}$ at 280 nm) in the peptide (when present) and/or absorbance of the bicinchoninic acid reagent (Pierce). The peptide solutions can be adjusted to the desired concentration and filter-sterilized prior to use.

FIGS. 2A-B illustrate the chemical structures of two embodiments of the present invention that were synthesized and purified according to the methods and procedures outlined above. The peptide constructs illustrated contain four identical sequences, each of which is connected to a branched central tri-lysine framework via a linker (GGGS, SEQ ID NO:9). FIG. 2A illustrates a peptide construct according to one embodiment of the present invention, a therapeutic peptide construct containing four copies of the core sequence HPSLK (SEQ ID NO:3). The peptide has a molecular mass of 3,685.2 Daltons. FIG. 2B illustrates another type of construct consisting of the construct shown in FIG. 2A, a therapeutic peptide containing four copies of the core sequence HPSLK (SEQ ID NO:3), to which a dansyl tag has been covalently added to the C-terminal β-alanine and cysteine residues. The molecular mass of the dansylated peptide is 4,165.8 Daltons.

Figure 3:
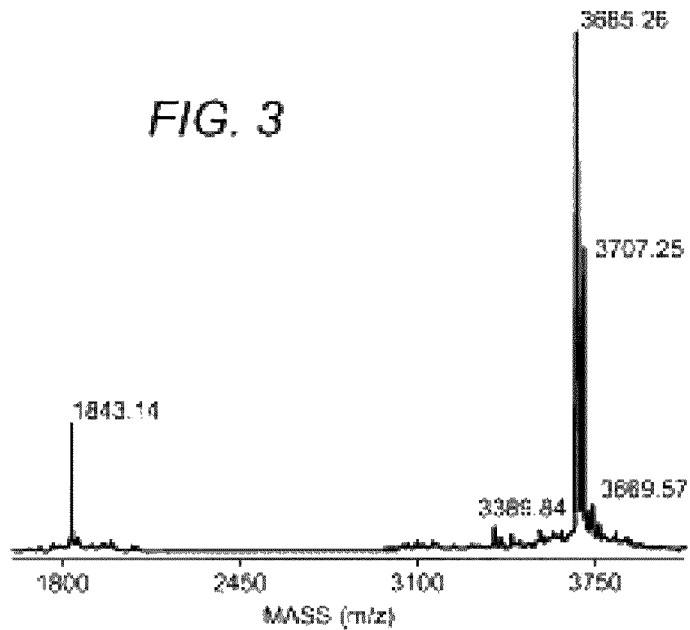
FIG. 3 is a mass spectrum of the peptide construct illustrated in FIG. 2A.
Figure 13A:
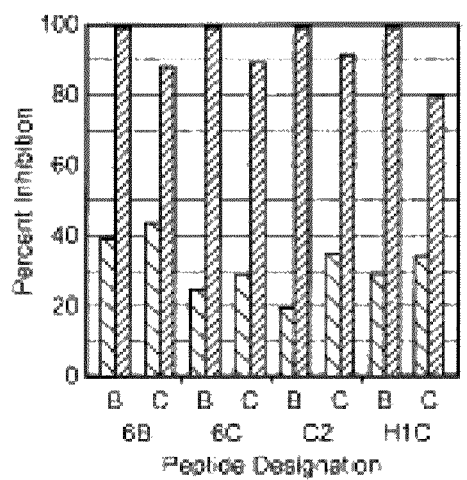
FIG. 13A is a vertical bar graph illustrating the synergistic inhibition of HIV-1 clade B (B) or HIV-1 clade C(C) replication in human blood cells by four peptide embodiments of the invention (peptides containing four copies of the core sequences HPSLK (SEQ ID NO:3; "6B"), PSSNA (SEQ ID NO:2; "6C"), VGGGS (SEQ ID NO:1; "C2"), and NPSHPLSG (SEQ ID NO:7; "H1C")) in either the absence (short bars) or in the presence (long bars) of an antibody preparation which, when assayed alone, provided only about 30% neutralization.
Figure 13B:
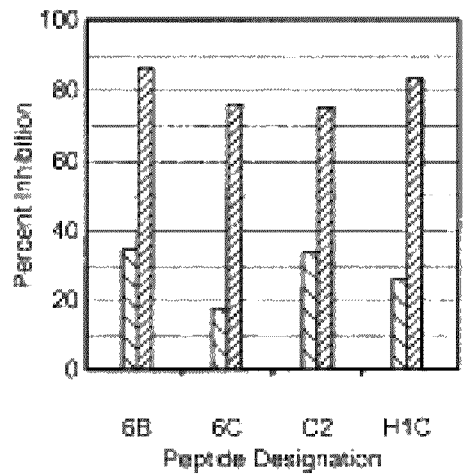
FIG. 13B is a vertical bar graph illustrating the synergistic inhibition of HIV-1 clade C replication in human blood cells by the four embodiments of the invention described in FIG. 13A in both the absence (short bars) or the presence (long bars) of an antibody preparation that, when assayed alone, provided no (about 0%) neutralization.

FIG. 3 illustrates a Matrix-Assisted Laser Desorption Ionization mass spectrum (MALDI-MS) of the purified construct containing four copies of the core sequence HPSLK (SEQ ID NO:3) whose structure is shown in FIG. 2A. The 3,707 Dalton component is a sodium adduct of the peptide construct which is generated during analysis by mass spectroscopy. The mass spectrum was recorded using a Voyager DE STR mass spectrometer (Applied Biosystems, Foster City, Calif.). Although these data indicate the peptides isolated were essentially pure, however, substantially or somewhat less purified peptides may also be suitable for use as therapeutic agents.

The peptides illustrated in FIGS. 2A-B are nonlimiting examples of a family of therapeutic peptides according to the present invention which typically have in common one or more of the following properties:

the ability to act synergistically with antibodies to neutralize HIV;

the N-terminal amino acid is usually hydrophobic and/or neutral;

the compositions are rich in proline, serine, threonine and asparagine;

the order of these amino acids in the sequences is not rigid and can vary;

a common sequence is XPSX, where X can be any amino acid;

the sequences vary in length from 4 to 8 amino acids;

the C-terminal amino acid can vary (e.g., HPSLK (SEQ ID NO:3), HPSLG (SEQ ID NO:4), HPSLL (SEQ ID NO:5), HPSLA (SEQ ID NO:6), etc.); and the internal amino acid sequences can vary (e.g., NPSHPLSG (SEQ ID NO:7), NPSHPSLG (SEQ ID NO:8), etc.).

Example 2

Lectin Binding

Four different assays were performed to demonstrate the binding affinity of the peptide constructs to various lectin proteins. Each assay used the same basic procedure. For lectins available as peroxidase conjugates, biotin-tagged peptides were added to streptavidin-coated wells of a microtiter plate (binding capacity, 125 pmoles per well, Pierce) and incubated 1 hr at room temperature. The wells were washed, blocked with 1% gelatin in 50 mM Tris-HCl (pH 7.5) containing 150 mM NaCl, 1 mM CaCl₂, 1 mM MgCl₂ and 1 mM MnCl₂ (buffer A) and washed two times with buffer A. Then 50 μL of 1 μg/mL horseradish peroxidase-conjugated lectins (Sigma-Aldrich, St. Louis, Mo.) in buffer A were added. After 1 hr incubation, wells were washed 4 times with buffer A and then 50 μL of peroxidase substrate (1-Step Ultra TMB-ELISA, Pierce) were added. Two to 10 min later the reaction was stopped with 50 μL 2 M H₂SO₄ and absorbance was read immediately at 450 nm. The amount of lectin bound was calculated from the specific activity of the peroxidase-conjugates (OD450/min/ng protein). The protocol was modified to assay binding of peptides to unconjugated lectins from *Sambucus nigra* (SNA1) and *Maackia amurensis* (MAA). Lectin-coated microwell strips (AlerCHEK, Portland, Me.) were hydrated in buffer A, blocked with 1% gelatin in buffer A, and then biotinylated peptide was added to each well. After 1 hr incubation, the wells were washed 3 times with buffer A and then 50 μL of 0.3 μg/mL peroxidase-conjugated streptavidin (Sigma-Aldrich) were added. Wells were washed 4 times with buffer A and peroxidase activity was assayed as previously described.

Figure 4:
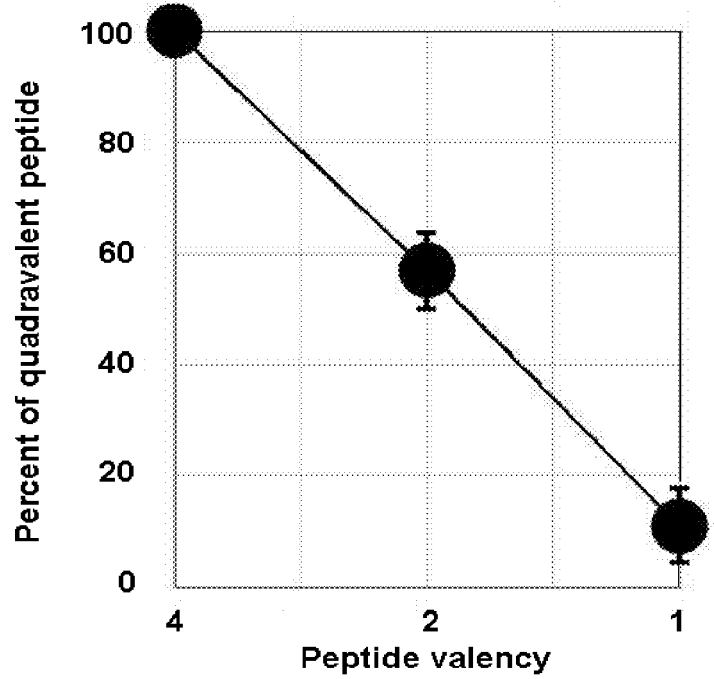
FIG. 4 is a line graph illustrating the binding activity of monovalent, bivalent, or quadravalent peptide constructs containing the core sequence HPSLK (SEQ ID NO:3) to seven different lectin proteins. The lectins (and the amount bound to the quadravalent peptide construct) were *Helix pomatia* (HP; 0.15 ng), *Griffonia simplicifolia* I-B4 (GS; 0.57 ng), *Dolichos biflorus* (DB; 2.0 ng), *Triticus vulgaris* (wheat germ agglutinin, WGA; 1.6 ng), *Sambucus nigra* (SNA1; (1.7 ng), *Maachia amurensis* (MAA; 1.9 ng) and concanavalin A (3.2 ng).

FIG. 4 illustrates the binding activity of peptide constructs with 1, 2, or 4 arms containing the core sequence HPSLK (SEQ ID NO:3) to various lectins. The assay contained 25 pmoles of the quadravalent peptide construct, 50 pmoles of the bivalent peptide construct, and 100 pmoles of the monovalent peptide to provide an equal number of HPSLK sequences per well. The data points are the ±SD from measurements with seven different lectins. The lectins (and the extent of binding of each to the quadravalent peptide) were *Helix pomatia* (HP; 0.15 ng), *Griffonia simplicifolia* I-B4 (GS; 0.57 ng), *Dolichos biflorus* (DB; 2.0 ng), *Triticus vulgaris* (wheat germ agglutinin, WGA; 1.6 ng), SNA1 (1.7 ng), MAA (1.9 ng) and concanavalin A (3.2 ng). As shown in FIG. 4, highest affinity was found with the quadravalent peptide, which was set as 100%. A bivalent peptide bound approximately half as strongly whereas the single sequence bound at a much lesser extent. The consistency of the results, with similar binding data regardless of the lectin, indicates a fundamental role of valency of the peptides in binding. This property is significant in terms of high affinity binding to receptors and consequent cross-linking of receptors, which is required to initiate a signal transduction cascade that leads to a cellular response.

Figure 5:
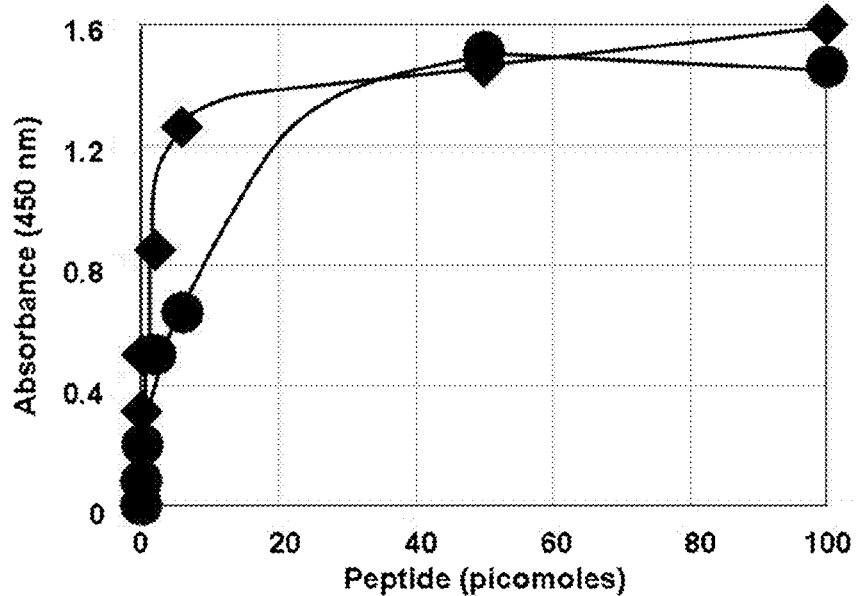
FIG. 5 is a line graph illustrating the avidity with which quadravalent peptide constructs containing the core sequences HPSLK (SEQ ID NO:3, diamond symbol) or NPSHPLSG (SEQ ID NO:7, circle symbol) bind to the SNA1 lectin.

FIG. 5 provides a demonstration of the avidity with which the quadravalent peptide constructs bind to lectins. Binding was measured by the amount of peroxidase-conjugated streptavidin that was retained in the wells after four washes. FIG. 5 depicts the binding of peptide constructs containing the core sequences HPSLK (SEQ ID NO:3, represented by the diamond symbol) or NPSHPLSG (SEQ ID NO:7, represented by the circle) to SNA1. Symbols indicate the average values of three experiments performed in quadruplicate. These results indicate that the peptide constructs bind to lectins with half-maximal binding in the low nanomolar concentration range.

Figure 6:
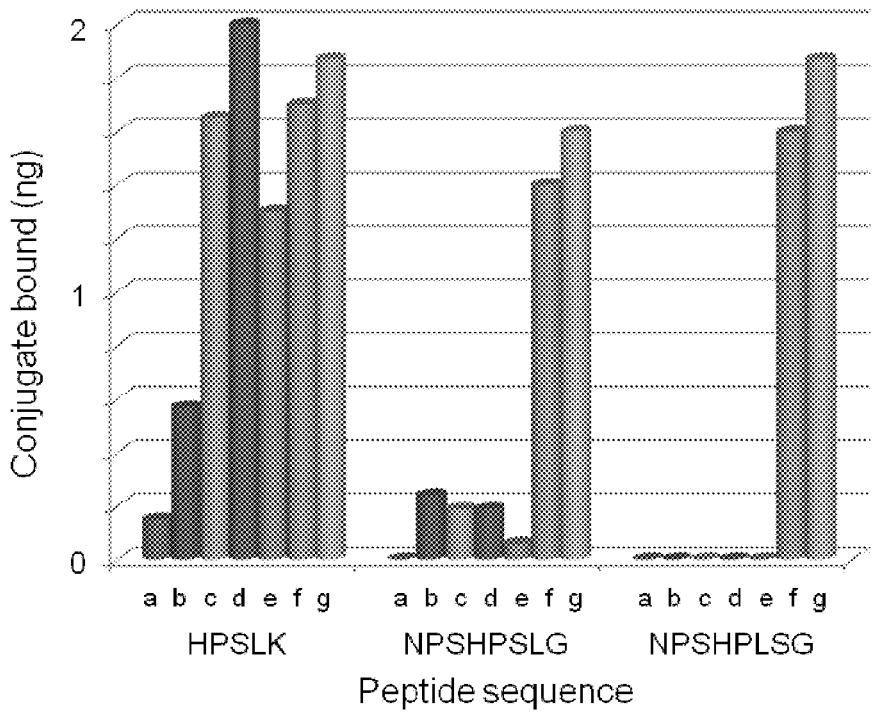
FIG. 6 is a vertical bar graph illustrating the binding of quadravalent peptide constructs containing the core sequence HPSLK (SEQ ID NO:3), NPSHPSLG (SEQ ID NO:8), or NPSHPLSG (SEQ ID NO:7) to lectins: (a), HP; (b), GS; (c), WGA; (d), DB; (e), *Ulex europaeus* (UEA1); (f), SNA1; (g), MAA.

FIG. 6 illustrates the specificity with which the quadravalent peptide constructs bind to different lectins. Binding activity of quadravalent peptide constructs containing the core sequences HPSLK (SEQ ID NO:3), NPSHPSLG (SEQ ID NO:8) or NPSHPLSG (SEQ ID NO:7) was measured for HP (specific for N-acetylgalactosamine and galactose), GS (specific for galactose), WGA (specific for N-acetylglucosamine and 5-acetylneuraminic acid), DB (specific for N-acetylgalactosamine), *Ulex europaeus* (UEA1, specific for L-fucose(α1-2)-D-galactose containing oligosaccharides), SNA1 (specific for 5-acetylneuraminic acid(α2-6)galactose/N-acetylgalactosamine) and MAA (specific for 5-acetylneuraminic acid(α2-3)galactose(β1-4)N-acetylglucosamine/glucose). Peptide constructs containing four copies of NPSHPSLG (SEQ ID NO:8) and NPSHPLSG (SEQ ID NO:7) bound specifically to SNA1 and MAA, lectins which bind oligosaccharides but not monosaccharides. The peptide construct containing four copies of HPSLK (SEQ ID NO:3) bound those lectins as well as lectins that bind to monosaccharides.

Figure 7:
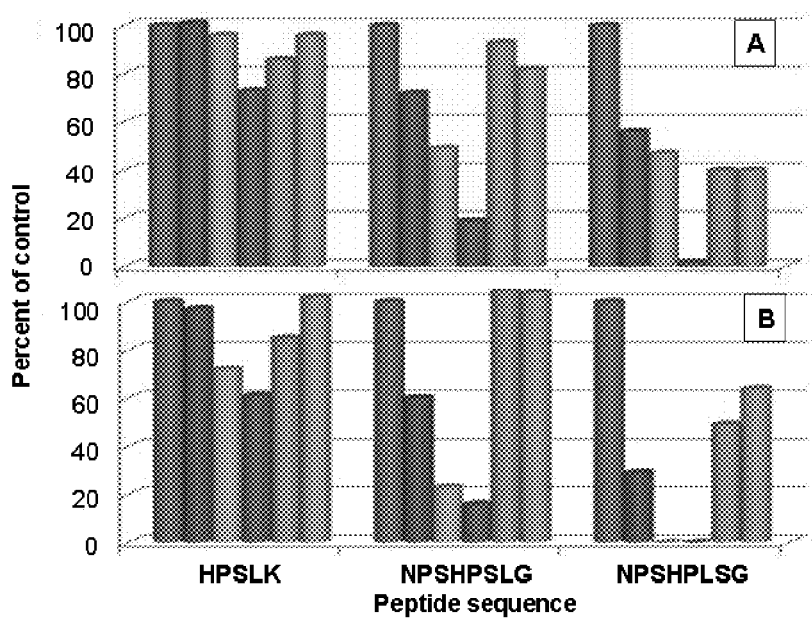
FIG. 7A is a vertical bar graph illustrating the inhibitory effect of fetuin and after digestion of fetuin with α-neuraminidase and β-galactosidase on the binding of quadravalent peptide constructs containing the core sequence HPSLK (SEQ ID NO:3), NPSHPSLG (SEQ ID NO:8), or NPSHPLSG (SEQ ID NO:7) to the SNA1 lectin. The table at the top of the figure indicates the amount of fetuin added relative to the peptide constructs, of which 100 pmoles were added to each well.
FIG. 7B is a vertical bar graph illustrating the inhibitory effect of fetuin and after digestion of fetuin with α-neuraminidase and β-galactosidase on the binding of quadravalent peptide constructs containing the core sequence HPSLK (SEQ ID NO:3), NPSHPSLG (SEQ ID NO:8), or NPSHPLSG (SEQ ID NO:7) to the MAA lectin. The table at the top of the figure indicates the amount of fetuin added relative to the peptide constructs, of which 100 pmoles were added to each well.

In another experiment, fetuin, a glycoprotein with glycan structures to which SNA1 and MAA are specific, was used to demonstrate that the peptide constructs interact with the glycan-binding site on the proteins. Fetuin (Calbiochem, La Jolla, Calif.) was digested with recombinant α-(2→3,6,8,9)-neuraminidase from *Arthrobacter ureafaciens* and β-(1→3, 4,6)-galactosidase, a mixture from *Streptococcus pneumoniae* and *Xanthomonas* sp., which were obtained from Sigma-Aldrich and used according to the supplier's instructions. FIG. 7A-B illustrates the inhibition of peptide constructs containing four copies of HPSLK (SEQ ID NO:3), NPSHPSLG (SEQ ID NO:8), or NPSHPLSG (SEQ ID NO:7) binding to SNA1 (FIG. 7A) and MAA (FIG. 7B) by fetuin, and after digestion of fetuin with α-neuraminidase and β-galactosidase. These data demonstrate that fetuin strongly inhibited the binding of the peptide constructs in a dose-dependent manner, indicating competition for the binding site. Further demonstration of competition for the binding site was obtained by enzymatically removing the terminal sugars from the glycans of fetuin that are involved in binding to the lectin.

Example 3

Stimulation of Phagocytosis by Peptides

Figure 8:
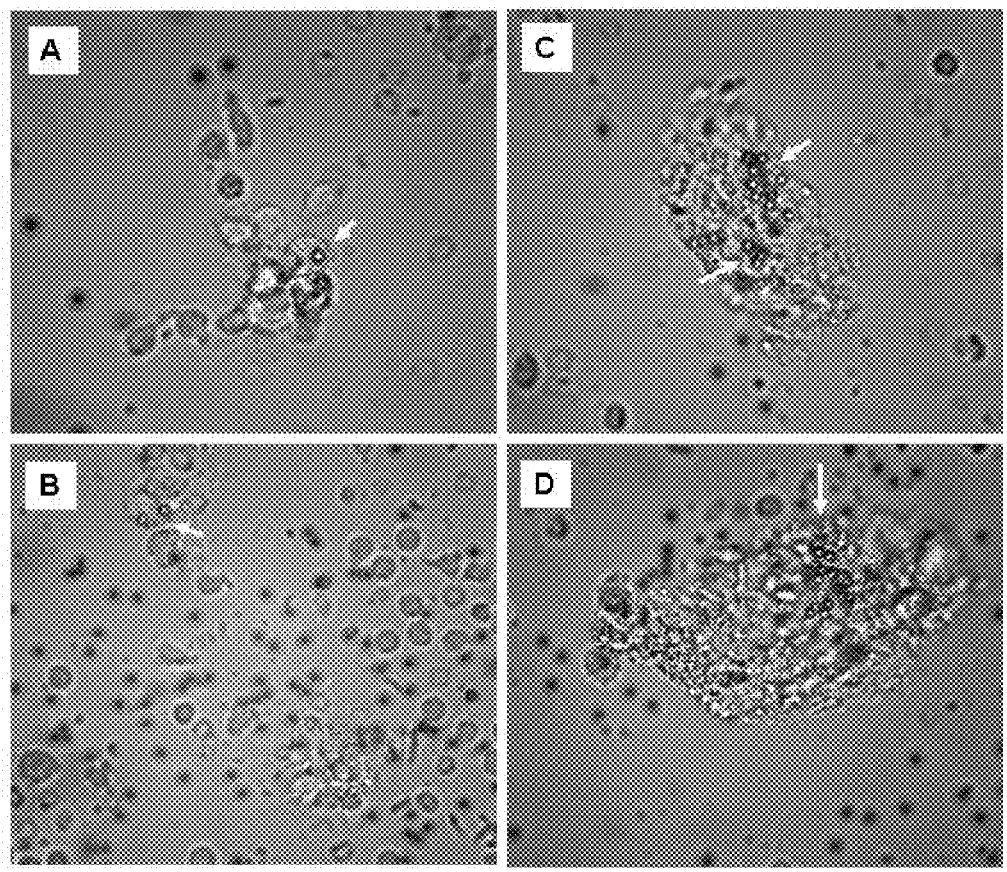
FIG. 8A is a micrograph depicting the phagocytosis of microspheres opsonized with anti-HIV antibodies in a control sample not treated with a therapeutic peptide. Arrows point to intracellular beads.
FIG. 8B is another micrograph depicting the phagocytosis of microspheres opsonized with anti-HIV antibodies in a control sample not treated with a therapeutic peptide. Arrows point to intracellular beads.
FIG. 8C is a micrograph depicting the phagocytosis of microspheres opsonized with anti-HIV antibodies in a sample treated with a therapeutic peptide containing four copies of the core sequence PSSNA (SEQ ID NO:2). Arrows point to intracellular beads.
FIG. 8D is a micrograph depicting the phagocytosis of microspheres opsonized with anti-HIV antibodies in a sample treated with a therapeutic peptide containing four copies of the core sequence NPSHPSLG (SEQ ID NO:8). Arrows point to intracellular beads.

The ability of the peptide constructs to stimulate phagocytosis was assessed in two experiments. In the first experiment, a biotin-tagged peptide epitope of a surface protein of HIV-1 was bound to streptvidin on the surface of the beads. An antibody preparation that was raised against this epitope was then bound to the HIV peptide. The beads were then washed and presented to peripheral blood mononuclear cell (PBMC) cultures pretreated with peptides. FIGS. 8A-B show that macrophages in cultures not treated with peptides had little, if any, phagocytic activity. In multiple control cultures, the number of beads within a macrophage-like cell ranged from 0 to 3. FIGS. 8C-D show cells treated with therapeutic peptide constructs containing four copies of the core sequence PSSNA (SEQ ID NO:2), and therapeutic peptide constructs containing four copies of the core sequence NPSHPSLG (SEQ ID NO:8) respectively. In the treated cultures, greater than 20 beads were counted in each phagocytic cell. After several subsequent and similar experiments were conducted, a phagocytic index was developed for the activity of macrophages to ingest microspheres opsonized with anti-HIV antibodies (TABLE 1).

TABLE 1

Relative index for phagocytosis of microspheres opsonized with anti-HIV antibodies by macrophages in PBMC cultures treated with each of the peptides.

| Peptide | Phagocytosis Index* |
|---|---|
| VGGGS, SEQ ID NO: 1 | +++ |
| HPSLK, SEQ ID NO: 3 | ++++ |
| PSSNA, SEQ ID NO: 2 | +++ |
| NPSHPLSG, SEQ ID NO: 7 | ++ |
| NPSHPSLG, SEQ ID NO: 8 | ++++ |
| INF-γ | +++ |
| None | (+) |

*Phagocytosis index is the number of ingested IgG-coated beads per sample.
(+) ≦3,
+ = 5,
++ = 10,
+++ = 15,
++++ ≧20.

In a second experiment, streptavidin-coated microspheres, dyed with Dragon Green (0.97 μm diameter, Bangs Laboratories, Inc., Fishers, Ind.) were opsonized with rabbit anti-streptavidin serum (Sigma-Aldrich) and washed with phosphate buffered saline, pH 7.4 (PBS). Human PBMCs were cultured in microtiter plates in RPMI-1640 medium containing 10% fetal bovine serum (FBS) and 1:100 dilution of penicillin-streptomycin solution (Mediatech, Inc., Herndon, Va.) Cultures were washed to remove non-adherent cells, and fresh medium containing FBS, antibiotics, and 50 nM peptide was added to adherent cells for an additional 20 to 24 h. Microspheres were added at approximately a 10:1 ratio to total cells, and after an additional 30 to 60 min of incubation, a solution containing 2% formalin was added. The samples were allowed to stand at 4° C. overnight, then washed 3 times with PBS to remove free microspheres and examined using a Nikon inverted microscope with a 40× objective lens.

Figure 9:
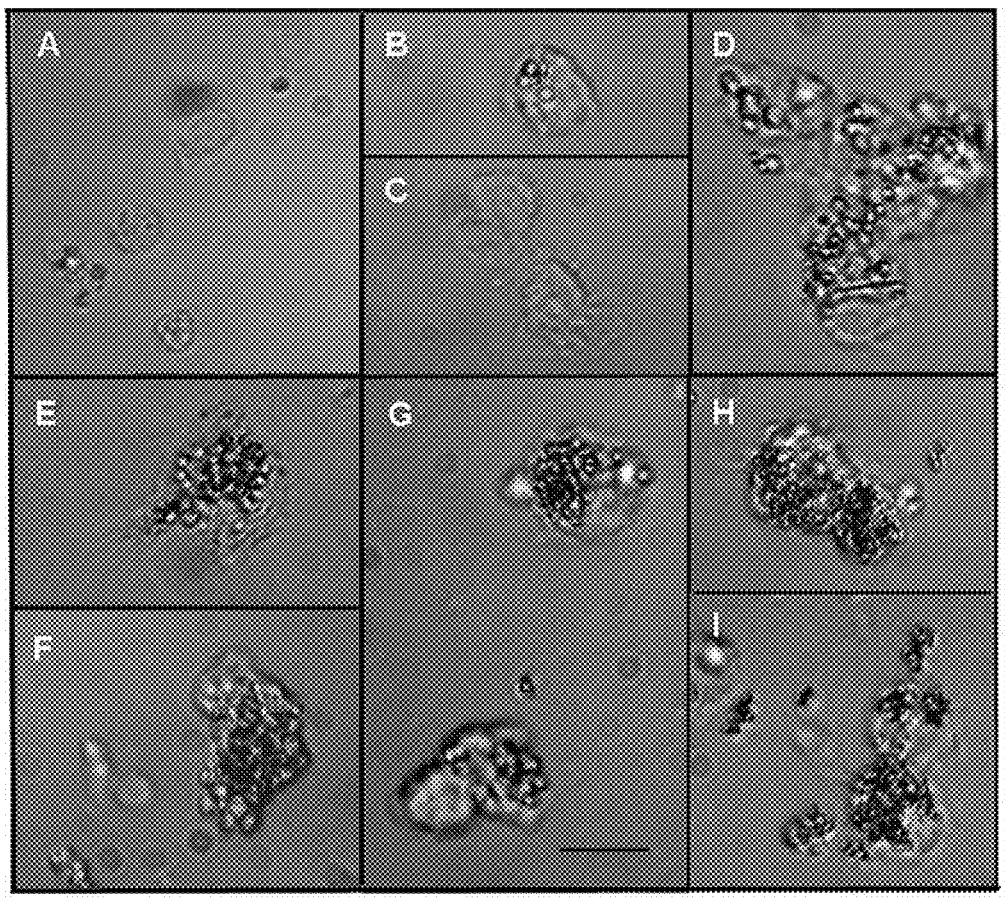
FIG. 9A is a micrograph depicting phagocytosis of opsonized microspheres by peripheral blood mononuclear cells treated with the negative control vehicle alone. Bar=10 μm for all panels.
FIG. 9B is a micrograph depicting phagocytosis of opsonized microspheres by peripheral blood mononuclear cells treated with 50 nM of a quadravalent peptide construct containing the inactive control sequence VSNQH (SEQ ID NO:13). Bar=10 μm for all panels.
FIG. 9C is another micrograph depicting phagocytosis of opsonized microspheres by peripheral blood mononuclear cells treated with 50 nM of a quadravalent peptide construct containing the inactive control sequence VSNQH (SEQ ID NO:13). Bar=10 μm for all panels.
FIG. 9D is a micrograph depicting phagocytosis of opsonized microspheres by peripheral blood mononuclear cells treated with 100 ng/mL interferon-gamma (positive control). Bar=10 μm for all panels.
FIG. 9E is a micrograph depicting phagocytosis of opsonized microspheres by peripheral blood mononuclear cells treated with the 50 nM of the quadravalent peptide construct containing the core sequence HPSLK (SEQ ID NO: 3). Bar=10 μm for all panels.
FIG. 9F is another micrograph depicting phagocytosis of opsonized microspheres by peripheral blood mononuclear cells treated with the 50 nM of the quadravalent peptide construct containing the core sequence HPSLK (SEQ ID NO: 3). Bar=10 μm for all panels.
FIG. 9G is yet another micrograph depicting phagocytosis of opsonized microspheres by peripheral blood mononuclear cells treated with the 50 nM of the quadravalent peptide construct containing the core sequence HPSLK (SEQ ID NO: 3). Bar=10 μm for all panels.
FIG. 9H is a micrograph depicting phagocytosis of opsonized microspheres by peripheral blood mononuclear cells treated with the 50 nM of the quadravalent peptide construct containing the core sequence NPSHPLSG (SEQ ID NO: 7). Bar=10 μm for all panels.
FIG. 9I is another micrograph depicting phagocytosis of opsonized microspheres by peripheral blood mononuclear cells treated with the 50 nM of the quadravalent peptide construct containing the core sequence NPSHPLSG (SEQ ID NO: 7). Bar=10 μm for all panels.

FIGS. 9A-I illustrate phagocytosis of opsonized microspheres by peptide-treated PBMCs. FIGS. 9A-C show negative controls of the vehicle alone (FIG. 9A) or cells treated with 50 nM of a peptide construct containing four copies of an inactive core sequence VSNQH (SEQ ID NO:13) (FIGS. 9B-C). FIG. 9D shows cells treated with 100 ng/mL interferon-gamma as the positive control. FIGS. 9E-G show cells treated with 50 nM of the peptide construct containing four copies of HPSLK (SEQ ID NO:3), and FIGS. 9H-I show cells treated with 50 nM of the peptide construct containing four copies of NPSHPLSG (SEQ ID NO:7). This procedure was performed four times, with different antibodies, and each time similar results were achieved. The experiment was quantified by counting the number of beads in the phagocytic cells (TABLE 2).

TABLE 2

Phagocytosis of microspheres opsonized with rabbit antiserum raised against HIV-1 gp41 envelope protein treated with a negative control, positive control, or therapeutic quadravalent peptide constructs.

| Treatment | Beads/cell (mean ± SD) | p value* |
|---|---|---|
| Vehicle | 1 ± 0.5 | — |
| VSNQH (SEQ ID NO: 13) | 1.3 ± 1.8 | 0.702 |
| Interferon-gamma | 35.8 ± 12.6 | 0.00016 |
| HPSLK (SEQ ID NO: 3) | 37.1 ± 6.8 | 0.00001 |
| NPSHPLSG (SEQ ID NO: 7) | 17.7 ± 6.0 | 0.00014 |

*Uptake of beads in cells treated with a quadravalent peptide construct containing the inactive core sequence VSNQH (SEQ ID NO: 13) was not significantly different from the vehicle control (p = 0.702). Paired Student's t-test analyses provided p values for the other treatments compared with the control quadravalent peptide containing the inactive core sequence VSNQH (SEQ ID NO: 13).

Figure 10:
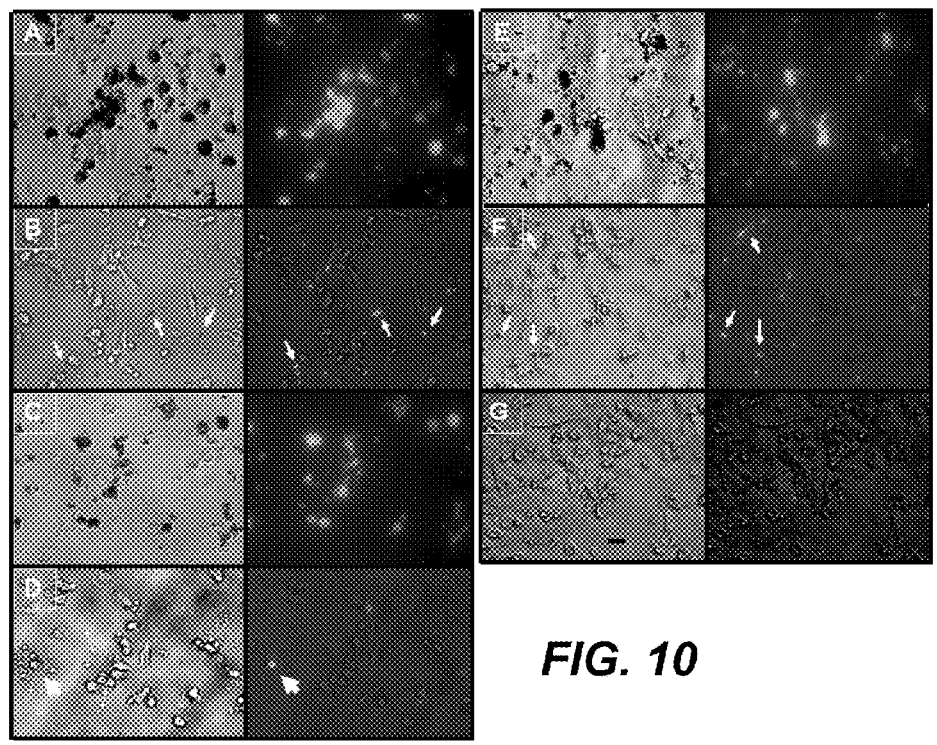
FIG. 10A is an electron micrograph depicting phagocytosis of opsonized microspheres by peripheral blood mononuclear cells treated with 50 nM of the quadravalent peptide construct containing the core sequence HPSLK (SEQ ID NO:3). Cells were examined by phase contrast microscopy (left panel) and fluorescence microscopy with blue excitation light (right panel)
FIG. 10B is an electron micrograph depicting phagocytosis of opsonized microspheres by peripheral blood mononuclear cells treated with 50 nM of the quadravalent peptide construct containing the core sequence HPSLK (SEQ ID NO:3) plus wortmannin. Cells were examined by phase contrast microscopy (left panel) and fluorescence microscopy with blue excitation light (right panel), and arrows indicate microspheres that remained in the extracellular medium.
FIG. 10C is an electron micrograph depicting phagocytosis of opsonized microspheres by peripheral blood mononuclear cells treated with 50 nM of the quadravalent peptide construct containing the core sequence NPSHPLSG (SEQ ID NO:7). Cells were examined by phase contrast microscopy (left panel) and fluorescence microscopy with blue excitation light (right panel)
FIG. 10D is an electron micrograph depicting phagocytosis of opsonized microspheres by peripheral blood mononuclear cells treated with 50 nM of the quadravalent peptide construct containing the core sequence NPSHPLSG (SEQ ID NO:7) plus wortmannin. Cells were examined by phase contrast microscopy (left panel) and fluorescence microscopy with blue excitation light (right panel), and arrowheads indicate microspheres that remained in the extracellular medium which were internalized by the cell cultures.
FIG. 10E is an electron micrograph depicting phagocytosis of opsonized microspheres by peripheral blood mononuclear cells treated with 50 nM of the quadravalent peptide construct containing the core sequence NPSHPSLG (SEQ ID NO:8). Cells were examined by phase contrast microscopy (left panel) and fluorescence microscopy with blue excitation light (right panel)
FIG. 10F is an electron micrograph depicting phagocytosis of opsonized microspheres by peripheral blood mononuclear cells treated with 50 nM of the quadravalent peptide construct containing the core sequence NPSHPSLG (SEQ ID NO:8) plus wortmannin. Cells were examined by phase contrast microscopy (left panel) and fluorescence microscopy with blue excitation light (right panel), and arrows indicate microspheres that remained in the extracellular medium.
FIG. 10G is an electron micrograph depicting phagocytosis of opsonized microspheres by peripheral blood mononuclear cells treated with 50 nM of the quadravalent peptide construct containing the inactive core sequence VSNQH (SEQ ID NO:13). Cells were examined by phase contrast microscopy (left panel) and fluorescence microscopy with blue excitation light (right panel)

In order to establish that the bead-like material within the cells was indeed engulfed beads, fluorescence was examined. The beads, impregnated with the Dragon Green dye, fluoresced when excited with blue light. Fluorescent images were captured by Metamorph software (Molecular Dynamics, Sunnyvale, Calif.) using the same microscope and lens described above. FIGS. 10A-10G show the results of this experiment. Cells were examined by both phase contrast microscopy (left panels) and fluorescence microscopy with blue excitation light (right panels). Also shown is the inhibition of bead uptake by a specific inhibitor of phagocytosis, wortmannin. FIG. 10A shows cells treated with the quadravalent peptide construct containing HPSLK (SEQ ID NO:3); FIG. 10B shows cells treated with the quadravalent peptide construct containing HPSLK (SEQ ID NO:3) plus wortmannin; FIG. 10C shows cells treated with the quadravalent peptide construct containing NPSHPLSG (SEQ ID NO:7); FIG. 10D shows cells treated with the quadravalent peptide construct containing NPSHPLSG (SEQ ID NO:7) plus wortmannin; FIG. 10E shows cells treated with the quadravalent peptide construct containing NPSHPSLG (SEQ ID NO:8); FIG. 10F shows cells treated with the quadravalent peptide construct containing NPSHPSLG (SEQ ID NO:8) plus wortmannin; and FIG. 10G shows cells treated with a quadravalent peptide construct containing an inactive core sequence VSNQH (SEQ ID NO:13). A few microspheres remained in the extracellular medium in wortmannin-treated cultures (arrows), and cells were occasionally found in these cultures that had internalized microspheres (D, arrowheads). As shown in FIGS. 10A, C, and E, cells containing beads were highly fluorescent.

Example 4

Signal Transduction

As demonstrated in the Example 3, the therapeutic peptide constructs elicit a strong phagocytic response in cells. Phagocytic cells are stimulated by two major mechanisms that involve the JAK/STAT regulatory pathway. The first is an inflammation-induced response to an environmental factor, which is characterized by an increased phosphorylation of the regulatory protein STAT2. The second is the so-called alternative activation pathway that does not involve an inflammatory agent. The latter pathway is stimulated by interleukin-4 and interleukin-13 and is characterized by an increased phosphorylation of STAT6. An experiment was performed to demonstrate that the peptide constructs can stimulate phagocytosis without inducing the release of inflammatory cytokines or causing systemic inflammation.

Peripheral blood mononuclear cells in RPMI-1640 medium, supplemented with 2 mM glutamine and 0.1% ovalbumin (Sigma-Aldrich), were plated at a density of $1 \times 10^5$ cells (250 µL) on 0.45 µm MultiScreen HTS HV sterile filter plates (Millipore) and incubated overnight at 37° C., 5% $CO_2$. Peptide constructs were added to 50 nM final concentration and incubated for 10 min. Phosphorylation of STAT2 and STAT6 was measured with a FACE STAT kit (Active Motif, Carlsberg, Calif.) according to the supplier's instructions. Briefly, the incubation was stopped by fixation with 25 µL of 37% formaldehyde (4% final concentration) for 20 min. Fixed cells were washed 3 times with PBS containing 0.1% Triton X-100 (wash buffer) and then incubated with 100 µL wash buffer containing 1% $H_2O_2$ and 0.1% azide for 20 min to inactivate cellular peroxidase activity. Non-specific binding sites were blocked with 100 µL of 3% bovine serum albumin in PBS for 1 hr. Primary antibody, at a 1:500 dilution, was incubated with cells overnight at 4° C. and the wells were then washed 2 times. Peroxidase-conjugated secondary antibody, at a 1:2000 dilution, was added and incubated for 1 hr at room temperature. Wells were washed 4 times and then 100 µL peroxidase substrate (Active Motif) was added. The reaction was stopped with 100 µL 2 M $H_2SO_4$ when sufficient blue color had developed. Absorbance was read immediately at 450 nm with a microtiter plate reader. Primary antibodies are specific for phosphorylated tyrosine-689 of STAT2 or phosphorylated tyrosine-641 of STAT6. Antibodies for total STAT2 and STAT6 recognize the proteins regardless of phosphorylation state.

The quadravalent peptide construct containing the core sequence HPSLK (SEQ ID NO:3), which binds lectins specific for monosaccharides and oligosaccharides (FIG. 6) stimulates phosphorylation of STAT2 (FIG. 11A) and STAT6

Figure 11:
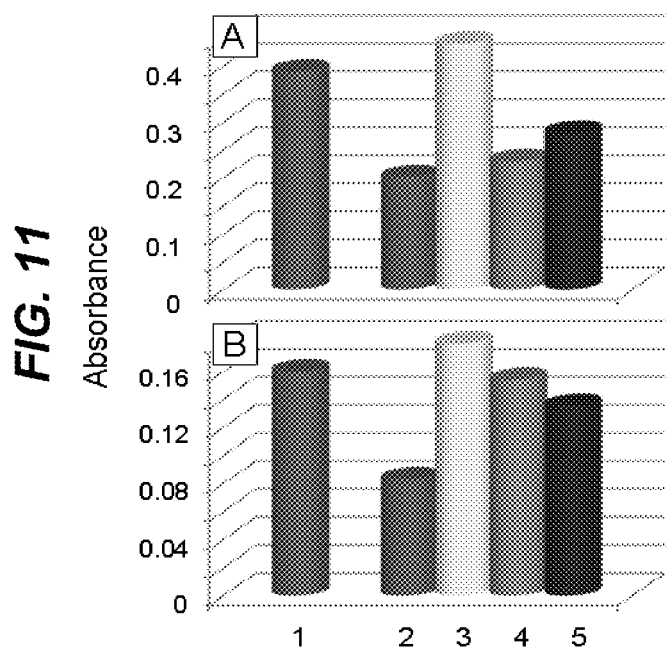
FIG. 11A is a three-dimensional vertical bar graph illustrating phosphorylation of STAT2 where bar (1) represents total STAT, bar (2) represents phospho-STAT in untreated cultures, bar (3) represents phosphorylated STAT2 in cells treated with 50 nM of the quadravalent peptide construct containing the core sequence HPSLK (SEQ ID NO:3), bar (4) represents phosphorylated STAT2 in cells treated with 50 nM of the quadravalent peptide construct containing the core sequence NPSHPLSG (SEQ ID NO:7), and bar (5) represents phosphorylated STAT2 in cells treated with 50 nM of the quadravalent peptide construct containing the core sequence NPSHPSLG (SEQ ID NO:8)
FIG. 11B is a three-dimensional vertical bar graph illustrating phosphorylation of STAT6 where bar (1) represents total STAT, bar (2) represents phospho-STAT in untreated cultures, bar (3) represents phosphorylated STAT6 in cells treated with 50 nM of the quadravalent peptide construct containing the core sequence HPSLK (SEQ ID NO:3), bar (4) represents phosphorylated STAT6 in cells treated with 50 nM of the quadravalent peptide construct containing the core sequence NPSHPLSG (SEQ ID NO:7), and bar (5) represents phosphorylated STAT6 in cells treated with 50 nM of the quadravalent peptide construct containing the core sequence NPSHPSLG (SEQ ID NO:8)

(FIG. 11B). In contrast, quadravalent peptide constructs containing the core sequences NPSHPLSG (SEQ ID NO: 7) or NPSHPSLG (SEQ ID NO:8), which bind only to lectins specific for oligosaccharides (FIG. 6), stimulated phosphorylation of STAT6 (FIG. 11B) more strongly than that of STAT2 (FIG. 11A).

Example 5

Synergy Between Antibodies and Peptides

The ability of the peptides to inhibit replication of HIV, both alone and in combination with antibodies, was tested as follows. Approximately 3 million cells of frozen human PBMCs, obtained from the California Blood Bank system, were thawed at 37° C. and transferred to a 50 mL conical tube where 8 mL of wash medium were added slowly. Then an additional 8 mL of wash medium were added and swirled to mix. The cells were then centrifuged at 330 g for 10 min, the supernatant was removed and the pellet was resuspended in 10 mL wash medium and centrifuged as above. The washed cells were then resuspended in RPMI-B medium containing 10% FBS, phytohemagglutin was added to 5 μg/mL, and cells were incubated at 37° C. for 24 hr in humidified 5% $CO_2$. Cells were washed, suspended to about 6 million cells per mL, and 50 μL, (about 250,000 viable cells) were added to each test well. Then 100 ↑L of the test peptide were added at a concentration sufficient to provide the desired final concentration, followed by 100 μL of virus suspension (100 median tissue culture infective doses (TCID50s)). The assay plate was incubated 3 days at 37° C., then washed 3 times to remove unbound virus, and the cells were again suspended to 250 μL of medium. After an additional 24 hr of incubation, cells were lysed with Triton X-100 and each sample was assayed by an enzyme-linked immunoassay for virus protein p24 to quantify neutralization of virus. In another set of samples, antibody preparations were also added at a desired concentration (i.e., in addition to peptide).

FIGS. 12A-12D are scatter plots illustrating the inhibition of HIV replication (neutralization) in PBMCs by the peptide construct containing four copies of the core sequence HPSLK (SEQ ID NO:3) linked to a branched central framework structure. This peptide construct was assayed for activity with two strains of HIV, clade B (Strain SF162) and clade C (Strain 97ZA009), both of which were provided by the California Department of Public Health (Richmond, Calif.). HIV-1 clade B is the major strain in North America and HIV-1 clade C is the major strain in central and southern Africa, India and China. The peptide was assayed either alone (−) or in combination with serum from HIV-infected individuals (+), as outlined below in TABLE 3.

TABLE 3

| FIG. | HIV Strain | Peptide | Serum |
|---|---|---|---|
| 5A | clade B | HPSLK (SEQ ID NO: 3) | + |
| 5B | clade B | HPSLK (SEQ ID NO: 3) | − |
| 5C | clade C | HPSLK (SEQ ID NO: 3) | + |
| 5D | clade C | HPSLK (SEQ ID NO: 3) | − |

In the absence of peptide, the antibody preparation (serum) provided only about 30% neutralization at the same dilution (data not shown).

The data shown in FIGS. 12A-12D indicate that the peptides have substantial inhibitory activity when assayed alone. The therapeutic peptide construct containing four copies of the core sequence HPSLK (SEQ ID NO:3), shows particularly strong inhibitory activity at the higher concentrations. However, even at low (picomolar) peptide concentrations, the peptides achieved essentially complete inhibition of viral replication in the presence of antibodies (serum), as shown in FIGS. 12A and 12C. Therefore, the peptides alone at picomolar and nanomolar concentrations achieved inhibition of replication (about 20 to about 40%) and the antibodies alone gave only modest or minimal attenuation of viral replication (about 30%).

In contrast, the peptides achieved nearly quantitative inhibition of viral replication when used in combination with the antibodies, particularly with antibodies from infected individuals. For assays in which antibodies against HIV were combined with the peptides, essentially complete inhibition of replication was achieved. Furthermore, a maximal extent of neutralization was obtained with the lowest concentration of peptide tested, indicating that the peptides are active in the nanomolar concentration range. The antibodies were provided as serum from HIV-infected patients by the California Department of Public Health (Richmond, Calif.) and diluted to a concentration which, in the absence of the peptides (data not shown), provided only about 30% neutralization.

FIG. 13A and FIG. 13B are vertical bar graphs illustrating the synergistic inhibition of HIV-1 clade B (B) and HIV-1 clade C(C) replication in human PBMCs by four different peptide embodiments of the present invention, the peptide constructs containing four copies of the core sequence HPSLK (SEQ ID NO:3), PSSNA (SEQ ID NO:2), VGGGS (SEQ ID NO:1) and NPSHPLSG (SEQ ID NO:7). The short bars represent neutralization by peptide alone. The long bars represent neutralization when pooled serum from HIV-positive patients was added along with the peptide. The bars represent averages from two experiments, each performed in quadruplicate. In one set of experiments, each peptide was assayed at 10 nM for the ability to inhibit replication. In the absence of peptide, the antibody preparation (serum) provided only about 30% neutralization (inhibition), at the same dilution (data not shown). The results of this first set of assays is shown in FIG. 13A. In a second set of experiments, peptide was added at 10 nM alone or in the presence of an anti-HIV-1 antibody preparation (gifted by Dr. Tsafrir Mor, The Biodesign Institute at Arizona State University, Tempe, Ariz.) which, in the absence of peptide, provided no neutralization (data not shown). The results from this second set of assays are shown in FIG. 13B. The data shown in FIGS. 13A and 13B indicate that all four peptide constructs displayed substantial inhibitory activity when assayed alone, that the level of inhibition was enhanced by adding antibodies, and that the therapeutic peptide construct containing four copies of HPSLK (SEQ ID NO:3) displayed the strongest inhibition of the four peptides assayed.

The data shown in FIGS. 12A-D and FIGS. 13A-B indicate that the peptides acted synergistically with the antibodies in the serum. Synergy between the peptides and antibodies is dramatically demonstrated in FIG. 13B, which illustrates results of an assay with a peptide added alone (short bars) or in combination with an antibody preparation that itself provided no neutralization (long bars). In combination with the peptide, 80% to 90% inhibition of replication was achieved.

In another experiment, the addition of a peptide to cultures of a T cell line (MT2) inhibited HIV replication from 5% to 35%, depending on the peptide. Addition of antiserum in these experiments did not show a synergistic effect (data not shown), nor was it expected because T cells do not perform antibody-mediated phagocytosis.

An additional experiment was performed in which PBMCs were prepared through Ficoll gradients from buffy coats purchased from the American Red Cross blood bank under IRB approval held by the blood bank. Aliquots of 5 to $10 \times 10^7$ cells were stored frozen in 90% FBS+10% DMSO in liquid $N_2$. Cells were thawed, sedimented, suspended in RPMI-1640 medium containing 25% FBS and 5% IL-2 (ZeptoMetrix Corp. Buffalo, N.Y.), and activated with 5 µg/ml phytohemagglutinin (PHA) for 24 hr at 37° C. in 5% $CO_2$. Cells were washed free of PHA, suspended in RPMI-1640 medium containing 10% FBS and IL-2, and then added to a 96-well microtiter plate (50 µL $2.5 \times 10^5$ cells/well). Peptide (100 µL) was added followed by 50 µL of medium or diluted HIV-positive serum, pooled from North American AIDS patients (final dilution 1:360). R5HIV-1 strain SF162 (clade B) or 97ZA009 (clade C) was then added (100 µL, 100 TCID50) and replication assayed according to a standard protocol (Wang et al., 1999). Cells were incubated 3 days at 37° C., then washed 3 times to remove free virus, peptide and antiserum and suspended to 250 µL of medium. After an additional 24-hr incubation, cells were lysed with Triton X-100 and protein p24 in each sample was assayed by ELISA to quantify the amount of virus (Eggink L L, Salas M, Hanson C V, Hoober J K. 2010. Peptide sugar mimetics prevent HIV Type 1 replication in peripheral blood mononuclear cells in the presence of HIV-positive antiserum. AIDS Research and Human Retroviruses 26:149-160).

Figure 14:
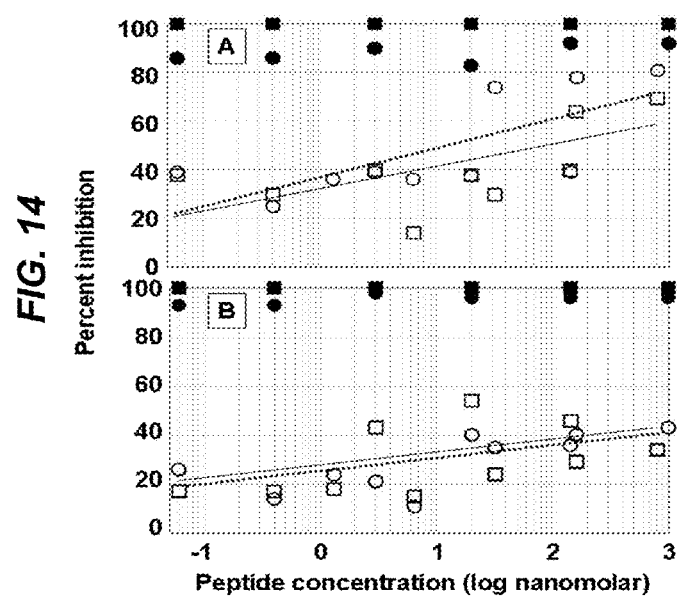
FIG. 14A is a line graph illustrating the percent inhibition of HIV-1 replication in peripheral blood mononuclear cells cultured with the quadravalent peptide construct containing the core sequence HPSLK (SEQ ID NO:3) at concentrations of 60 pM to 1 μM. Open symbols indicate values for cells cultured with the peptide construct alone, and filled symbols indicate values for cells culture with the peptide construct added with 1:360 dilution of serum from HIV-positive patients infected with a clade B virus. The circle symbol indicates percent inhibition of clade B (strain SF 162) and the square symbol indicates percent inhibition of clade C (strain 97ZA009)
FIG. 14B is a line graph illustrating the percent inhibition of HIV-1 replication in peripheral blood mononuclear cells cultured with the quadravalent peptide construct containing the core sequence NPSHPLSG (SEQ ID NO:7) at concentrations of 60 pM to 1 µM. Open symbols indicate values for cells cultured with the peptide construct alone, and filled symbols indicate values for cells culture with the peptide construct added with 1:360 dilution of serum from HIV-positive patients infected with a clade B virus. The circle symbol indicates percent inhibition of clade B (strain SF 162) and the square symbol indicates percent inhibition of Glade C (strain 97ZA009)

The peptide constructs alone inhibited HIV replication in cultures of PBMCs as high as 60 to 80% at concentrations of 1000 nM. In the presence of antiserum from HIV-positive patients, replication of the virus was inhibited 100% at peptide concentrations of 1 nM. FIG. 14 shows inhibition of HIV-1 replication in PBMCs cultured with the quadravalent peptide construct containing the core sequence HPSLK (SEQ ID NO:3, FIG. 14A) or NPSHPLSG (SEQ ID NO:7, FIG. 14B) at concentrations of 60 pM to 1 µM. Open symbols are the peptide constructs alone and filled symbols are the peptide constructs added with 1:360 dilution of serum from HIV-positive patients infected with a clade B virus (antiserum alone provided 30% inhibition). Circles represent clade B (strain SF 162) and squares represent clade C (strain 97ZA009). Lines for the peptide construct alone were generated by polynomial curve fitting (solid line=clade B, dotted line=clade C).

Therefore, the synergy demonstrated in FIGS. 12A-D, FIGS. 13A-B, and FIGS. 14A-B indicates a role of the peptide that can be separate from the potential action on lymphocytes. Clearly, the effect of the peptides can be more than a simple additive effect of the peptide plus antibodies, and very likely results from activation of phagocytes. Without such activation, one would not expect the virus-antibody complex to be effectively cleared via Fc-mediated phagocytosis by these cells.

Example 6

Induction of Cytokine Release

To determine whether inhibition of HIV replication by the peptide may be the result of induction of release of cytokines, cultured PBMCs were treated with one peptide embodiment of the present invention and, after 4 hr incubation, the medium was collected and assayed for changes in the amounts of 40 different cytokines. The therapeutic peptide construct containing four copies of the core sequence HPSLK (SEQ ID NO:3) shown in FIG. 2B was added at a concentration of 100 nM in each of the assays. Approximately 3 million cells of frozen human PBMCs were thawed at 37° C. and transferred to a 50 mL conical tube where 8 mL of wash medium were added slowly. Then an additional 8 mL of wash medium were added and swirled to mix. The cells were then centrifuged at 330 g for 10 min, the supernatant was removed and the pellet was resuspended in 10 mL wash medium and centrifuged as above. The washed cells were then resuspended in RPMI-1640 medium containing 10% FBS to about 6 million cells per mL and 100 µL of the suspension were added into each well of a 96-well microtiter plate and incubated overnight at 37° C. in humidified 5% $CO_2$. After 24 hr the medium was replaced with 200 µL fresh RPMI-1640 medium containing 10% FBS and incubated at 37° C. in humidified 5% $CO_2$ for 2 days. For the data shown in TABLE 4, the peptide aliquot was then added to samples in duplicate at a final concentration of 100 nM and incubated at 37° C. in humidified 5% $CO_2$ for 4 hr. For other experiments (data not included), the incubation was continued for 24 hr. The medium was then removed and stored at −80° C. The samples were analyzed for production of cytokines One set of control cells was not treated with an experimental agent. A second set of control cells was treated with LPS, an agent commonly used to induce production of a variety of inflammatory cytokines The positive control for inflammation was essential to ensure that the peptides did not produce an unregulated inflammatory response.

Culture medium was removed for assay of cytokine levels with methods developed by RayBiotech, Inc. (Norcross, Ga.). In this technology, membrane arrays of antibodies against cytokines were incubated with samples of media. After washing, the array was incubated with a cocktail of all antibodies tagged with biotin. The membrane was then washed free of unbound antibodies and incubated with streptavidin labeled with a fluorescent dye. After a final wash, the membrane arrays were read in a fluorescence detector.

The peptides did not cause cytotoxicity, as assayed by a double-dye method in which acridine orange fluoresces green in viable cells and ethidium bromide fluoresces red in dead cells. Toxicity of the peptide in vivo was tested by injection of a peptide into animals. The peptides can be administered in a number of ways, including without limitation by injection (intravenously, subcutaneously, intramuscularly or intraperitoneally, topically (transmucosally, transbuccally, or transdermally) and/or orally (liquid, tablet or capsule). In preliminary studies on mice, no adverse effects of the peptide have been observed (data not shown). In contrast, treated animals appear to exhibit enhanced well being, which might be a beneficial side effect of enhanced immunity in otherwise healthy subjects.

TABLE 4 contains data showing cytokines that are released at a significantly higher rate during a 4-hr incubation of PBMCs with the branched peptide construct in the presence of serum; that construct, whose structure is illustrated in FIG. 2B, contained four copies of the core sequence HPSLK (SEQ ID NO:3). Among these cytokines are IL-2, IL-4, IL-16, IL-17, TNF-β and TIMP-2. Several cytokines, in particular IL-16, IL-17, TNF-β and TIMP-2 show more than a two-fold increase over untreated control samples.

TABLE 4

Relative Cytokine Concentration after Incubation of PBMCs in Serum with Peptide Construct Containing Four Copies of the Core Sequence HPSLK (SEQ ID NO: 3).

| Cytokine | HPSLK (SEQ ID NO: 3) | Untreated | LPS |
|---|---|---|---|
| Increased: | | | |
| Eotaxin-2 | 562 | 193 | 469 |
| ICAM-1 | 87 | 57 | 53 |
| I-309 | 101 | 26 | 39 |
| IL-2 | 131 | 86 | 90 |
| IL-3 | 168 | 130 | 132 |
| IL-4 | 64 | 30 | 49 |
| IL-6 | 202 | 98 | 4375 |
| IL-16 | 10 | 1 | 2 |
| IL-17 | 27 | 5 | 10 |
| TNF-β | 117 | 38 | 95 |
| TIMP-2 | 230 | 58 | 92 |
| sTNF RI | 83 | 42 | 58 |
| sTNF RII | 30 | 8 | 26 |
| Decreased: | | | |
| IL-1α | 169 | 225 | 246 |
| IL-13 | 105 | 138 | 125 |
| IL-11 | 0 | 17 | 26 |
| IL-12p40 | 17 | 108 | 46 |
| IL-12p70 | 32 | 90 | 89 |

As shown in the example in TABLE 4, the peptide stimulated release of several important cytokines IL-2 activates T, B and natural killer cells and is used therapeutically. IL-4 promotes proliferation and differentiation of B-cells and inhibits production of inflammatory cytokines such as IL-1, IL-6 and TNF-α and should attenuate secretion of TNF-α as treatment continues. Furthermore, the stimulation of secretion of sTNF RI and sTNF RII, soluble forms of the receptor for TNF-α, an inflammatory cytokine, should mitigate its deleterious effects. Thus, an inflammatory response to treatment with the peptide may occur, but such inflammation will be transient. Stimulation of release of highly inflammatory cytokines, such as IL-1 and IL-6, was minimal. For example, in the experiment shown in TABLE 4, release of IL-6 was 202 (arbitrary units) in the experimental sample, 98 in the untreated sample, but 4,375 in the LPS-treated sample. IL-16 is secreted by CD8(+) cells (lymphocytes), is a natural ligand for CD4, and suppresses replication of HIV. IL-17 is produced by activated CD4(+) T cells, enhances expression of ICAM-1, IL-6, IL-8 and G-CSF, and is a mediator of angiogenesis.

Of particular importance, the peptide did not stimulate release of IL-10, a cytokine correlated with suppression of the TH1 immune system in HIV-infected individuals.

This pattern of cytokine release, with the indication of macrophage activation, provides real promise that the peptides of the present invention will be particularly well suited to treatment of HIV infections and other infectious diseases. In other embodiments of the invention, release of other beneficial cytokines such as IL-8 and IL-15 by PBMCs can be stimulated. In one embodiment, for example, the cytokines IL-8, IL-15, IL-16, RANTES or combinations thereof may be stimulated.

Therefore, the mixture of cytokines released from PBMCs in response to the peptides described herein should provide, either in isolation or in combination with other treatments, an effect therapy against HIV infections. Treatment with the peptides of the present invention should induce activation of cells of the immune system in vivo and provide a sustained endogenous elevation of beneficial cytokines, in contrast to the rapid disappearance of these proteins when given exogenously. In addition, the peptides of the present invention can also stimulate release of TNF-α, a marker of TH2-type macrophage activation. Although IL-8 and TNF-α are inflammatory, their secretion is a normal function of monocyte/macrophage activity and can be calibrated by the amount of peptide administered.

TABLE 5 is based on the same data as TABLE 4, and shows the effects of constructs containing four copies of VGGGS (SEQ ID NO:2), HPSLK (SEQ ID NO:3), PSSNA (SEQ ID:2) and NPSHPLSG (SEQ ID NO:7) on the relative concentrations of cytokines in the medium of PBMC cultures treated for 4 hr with each peptide construct as compared with untreated control cultures and LPS-treated cells. TABLE 5 also shows that several peptides increase release of IL-21, an important antiviral cytokine

TABLE 5

Relative concentrations of cytokines in PBMCs treated for 4 hr with each peptide construct as compared with untreated control cultures and LPS-treated cells. The absence of a number indicates no significant change as compared to the untreated control.

| | Core Sequence of Peptide | | | | | |
|---|---|---|---|---|---|---|
| Cytokine | VGGGS | HPSLK | PSSNA | NPSHPLSG | None | LPS |
| Eotaxin | | | | | 32 | 31 |
| Eotaxin-2 | | 562 | | 129 | 193 | 469 |
| GCSF | | | | | 108 | 120 |
| GM-CSF | | | | | 57 | 106 |

TABLE 5-continued

Relative concentrations of cytokines in PBMCs treated for 4 hr with each peptide construct as compared with untreated control cultures and LPS-treated cells. The absence of a number indicates no significant change as compared to the untreated control.

| | Core Sequence of Peptide | | | | | |
|---|---|---|---|---|---|---|
| Cytokine | VGGGS | HPSLK | PSSNA | NPSHPLSG | None | LPS |
| ICAM-1 | 89 | 87 | | | 57 | 53 |
| IFN-γ | | | | 191 | 134 | 158 |
| I-309 | | 101 | | | 26 | 39 |
| IL-1α | 291 | 169 | | | 225 | 246 |
| IL-1β | | | | | 44 | 47 |
| IL-2 | 125 | 131 | | | 86 | 90 |
| IL-3 | | 168 | | | 130 | 132 |
| IL-4 | | 64 | 60 | | 30 | 49 |
| IL-6 | | 202 | | | 98 | 4,375 |
| IL-6sR | | | | | 52 | 52 |
| IL-7 | | | | | 154 | 178 |
| IL-8 | | | 702 | 491 | 417 | 840 |
| IL-10 | | | | | 101 | 218 |
| IL-11 | | 0 | | 26 | 17 | 26 |
| IL-12p40 | 51 | 17 | 28 | 44 | 108 | 46 |
| IL-12p70 | | 32 | 69 | | 90 | 89 |
| IL-13 | | 105 | | | 138 | 125 |
| IL-15 | 130 | | 153 | | 97 | 104 |
| IL-16 | 10 | 10 | 12 | | 1 | 2 |
| IL-17 | 24 | 27 | 21 | 3 | 5 | 10 |
| IL-21 | | 95 | 130 | 115 | 50 | (IFN-γ: 100) |
| IP-10 | 321 | | | | 230 | 268 |
| MCP-1 | | 941 | | | 1,464 | 1,844 |
| MCP-2 | | | | | 56 | 177 |
| M-CSF | | | | | 44 | 59 |
| MIG | | | | | 54 | 66 |
| MIP-1a | | | | | 81 | 237 |
| MIP-1b | | | | | 1,172 | 1,828 |
| MIP-1d | | | | 82 | 40 | 38 |
| RANTES | 213 | | | | 80 | 114 |
| TGF-β1 | | | | | 62 | 62 |
| TNF-α | | | 123 | | 73 | 93 |
| TNF-β | 111 | 117 | | | 38 | 95 |
| sTNF RI | | 83 | | | 42 | 58 |

TABLE 5-continued

Relative concentrations of cytokines in PBMCs treated for 4 hr with each peptide construct as compared with untreated control cultures and LPS-treated cells. The absence of a number indicates no significant change as compared to the untreated control.

| Cytokine | Core Sequence of Peptide | | | | None | LPS |
|---|---|---|---|---|---|---|
| | VGGGS | HPSLK | PSSNA | NPSHPLSG | | |
| sTNF RII | 26 | 30 | 21 | | 8 | 26 |
| PDGF-BB | | | | | 43 | 56 |
| TIMP-2 | 205 | 230 | | | 58 | 92 |

Another important application of the present invention may be the use of the peptides as microbicides, which are preparations that can be formulated for transmucosal delivery, including without limitation gels, creams, films, or suppositories that can be applied in various combinations inside the vagina or rectum to protect against sexually transmitted infections including HIV. Microbial infections suitable for treatment according to the invention include without limitation bacterial, viral, protozoal, and fungal infections.

In addition to its therapeutic potential for treatment, the technology of the present invention can be used for other applications, including application as a preliminary in vitro test prior to therapy. The immune system of a HIV-infected person is apparently incapable of maintaining a long-term defense against the infection. The causes of viral escape from the immune system could be (1) the result of mutations in the viral genome which render the virus epitope-free and thus not subject to binding by an antibody, or (2) the phagocytic cells that are responsible for eliminating the virus-antibody complex are quiescent. To discriminate between these possibilities, samples of blood from an individual infected with a virus such as HIV could be incubated with and without addition of a peptide of the present invention. In the former case, the synergistic activity of the peptides would not be achieved when viral epitopes to which antibodies bind are not present. However, in the latter case, the peptides could activate phagocytes and achieve elimination of the virus. Either way, the results would then be available to allow the decision of whether to proceed to treatment, and the results described in this document demonstrate the feasibility of this test.

The embodiments and examples set forth herein were presented in order to best explain the present invention and its practical application and to thereby enable those of ordinary skill in the art to make and use the invention. However, those of ordinary skill in the art will recognize that the foregoing description and examples have been presented for the purposes of illustration and example only. The description as set forth is not intended to be exhaustive or to limit the invention to the precise form disclosed. Many modifications and variations are possible in light of the teachings above without departing from the spirit and scope of the forthcoming claims. Although the examples herein disclose the therapeutic efficacy of the peptides of the present invention with respect to neutralizing replication of the HIV virus, for example, the peptides should also be useful to diagnose or treat a wide variety of infections or disorders, including prophylactic treatments for prevention of such maladies, and for enhancing or stabilizing the well being of healthy subjects. Furthermore, larger peptides containing active core sequences could potentially enhance the therapeutic benefits disclosed herein.

Example 7

Cytotoxicity of Peptides

Figure 15:
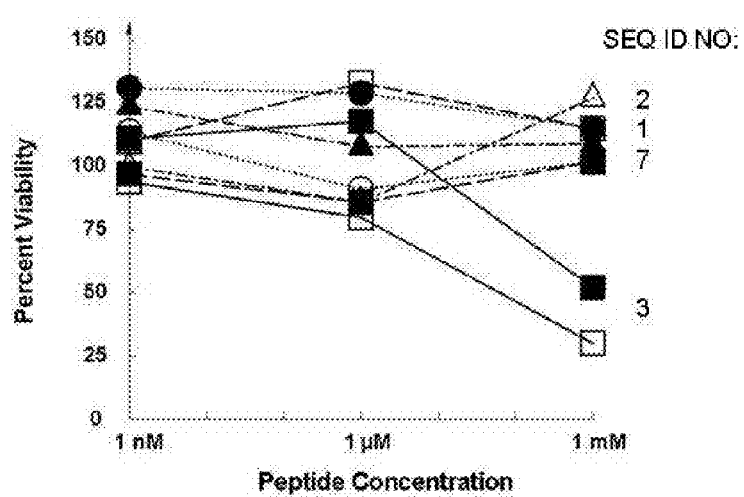
FIG. 15 is a line graph depicting the assay for cytotoxicity of peptides containing four copies of the core sequences HPSLK (SEQ ID NO:3), PSSNA (SEQ ID NO:2), VGGGS (SEQ ID NO:1), and NPSHPLSG (SEQ ID NO:7). Filled symbols indicate the quadravalent peptide construct was added in phosphate-buffered saline as vehicle, and open symbols indicate the quadravalent peptide construct was added in diluted HIV-positive antiserum as vehicle. Data are expressed as the ratio of viability of peptide-treated cells to cells that received only the vehicle.

The ability of peptides to reduce viability of cells in PBMC cultures was assayed by adding a range of concentrations and testing viability by dye uptake. PBMC cultures were incubated with the peptides for 72 hr each at the increasing concentrations of 1 nM, 1 μM and 1 mM. Ability of cells to exclude a dye was an indication of viability as viable cells express green fluorescence and non-viable cells express orange fluorescence. Only one of the peptides, the therapeutic peptide construct containing four copies of the core sequence (HPSLK SEQ ID NO:3), partially reduced viability when added at a concentration of 1 mM (FIG. 15). Because the peptides are active at concentrations below 1 nM, and the therapeutic range would be concentrations less than 100 nM, the toxic concentration is at least 1000- to 10.000-fold higher than an effective concentration. See FIG. 15 for the graphical results of the assay for cytotoxicity of quadravalent peptide constructs containing the core sequences HPSLK (SEQ ID NO:3), PSSNA (SEQ ID NO:2), VGGGS (SEQ ID NO:1), or NPSHPLSG (SEQ ID NO:7).

What is claimed is:

1. A polypeptide comprising multiple copies of a therapeutic peptide consisting of NPSHPLSG (SEQ ID NO: 7).

2. The polypeptide of claim 1, wherein the polypeptide comprises a construct and at least two arms, the construct having a central framework and each arm consisting of a core sequence linked to the central framework via a linker, wherein each core sequence is NPSHPLSG (SEQ ID NO: 7).

3. The polypeptide of claim 2, wherein the central framework consists of a tri-lysine core and the linker is selected from the group consisting of GGGS (SEQ ID NO: 9), GGGSGGGS (SEQ ID NO: 10), SSSS (SEQ ID NO: 11), and SSSSSSSS (SEQ ID NO: 12).

4. The polypeptide of claim 2, wherein the polypeptide comprises four arms.

5. A therapeutic composition comprising the polypeptide of claim 1, wherein the composition is immunostimulatory and further comprises an antigen of interest, the antigen being in an amount sufficient to stimulate antigen presentation to an immune system.

6. A method of treating a disease in which antibodies are produced against an antigen or invading pathogen, the method comprising:
   administering to the subject one or more polypeptides of claim 1 in an amount sufficient to increase production of antibodies produced against the antigen or invading pathogen in the subject, wherein the disease is cancer or is associated with the HIV retrovirus.

7. A method of inducing Fc-mediated phagocytosis in a subject, the method comprising administering to the subject one or more polypeptides of claim 1 in an amount sufficient to induce phagocytosis in the subject.

8. A method of enhancing a vaccination, comprising administering to a subject receiving a vaccination an effective amount of one or more polypeptides of claim 1, wherein the polypeptide is administered to the subject in conjunction with a vaccination and the polypeptide is in an amount sufficient to stimulate the immune system of the subject to the vaccination as compared to a control, the control being vaccination without the polypeptide present.

9. A method of modulating the cytokine expression in a subject, the method comprising administering to a subject one or more polypeptides of claim 1, wherein the polypeptide is in an amount sufficient to increase the expression of at least one endogenous cytokine selected from the group consisting of: Eotaxin-2, ICAM-1, I-309, IL-2, IL-3, IL-4, IL-8, IL-15, IL-16, IL-17, TNF-β, TIMP-2, RANTES, sTNF RI, and sTNF RII.

10. The method of claim 9, wherein the polypeptide is in an amount to decrease at least one endogenous cytokine selected from the group consisting of: IL-1α, IL-11, IL-12p40, and IL-12p70.

11. The method of claim 9, wherein the polypeptide does not substantially stimulate the release of IL-6.

12. A diagnostic method for evaluating the potential effectiveness of a treatment for a subject, the method comprising:
   incubating a blood and/or cell sample from a subject in vitro in the presence of at least one polypeptide according to claim 1 as a test sample;
   incubating the blood and/or cell sample from the subject in the absence of the at least one polypeptide as a control; and
   measuring whether there is an increase in immunogenic activity in the test sample as compared to the control, wherein an increase in immunogenic activity in the test sample is indicative of a potentially effective treatment for the subject.

13. The method of claim 12, wherein the increase of immunogenic activity includes an increase in phagocytic cell activity in the test sample.

14. A diagnostic method for evaluating the potential effectiveness of a treatment on a subject, the method comprising:
   incubating a blood and/or cell sample from a subject in vitro in the presence of at least one polypeptide according to claim 1; and
   measuring the production of cytokines released after incubation with the polypeptide to obtain cytokine release results or measuring the activity of phagocytic cells in the sample to obtain phagocytic activity results.

* * * * *